(12) United States Patent
Okita

(10) Patent No.: US 7,855,784 B2
(45) Date of Patent: Dec. 21, 2010

(54) SUBSTRATE PROCESSING METHOD, SUBSTRATE PROCESSING SYSTEM, PROGRAM, AND RECORDING MEDIUM

(75) Inventor: Shinichi Okita, Nishitokyo (JP)

(73) Assignee: Nikon Corporation, Tokyo (JP)

( * ) Notice: Subject to any disclaimer, the term of this patent is extended or adjusted under 35 U.S.C. 154(b) by 45 days.

(21) Appl. No.: 12/182,692

(22) Filed: Jul. 30, 2008

(65) Prior Publication Data

US 2009/0059217 A1    Mar. 5, 2009

Related U.S. Application Data

(63) Continuation of application No. PCT/JP2007/051555, filed on Jan. 31, 2007.

(30) Foreign Application Priority Data

Feb. 3, 2006    (JP) .............................. 2006-027045

(51) Int. Cl.
    *G01N 21/00* (2006.01)

(52) U.S. Cl. ................. 356/237.5; 356/237.1; 356/400; 356/622; 702/1; 702/81; 702/187

(58) Field of Classification Search ... 356/237.1–237.6, 356/400, 622; 702/1, 81, 187
    See application file for complete search history.

(56) References Cited

U.S. PATENT DOCUMENTS

2007/0219736 A1* 9/2007 Okita .......................... 702/81

* cited by examiner

*Primary Examiner*—Gregory J Toatley
*Assistant Examiner*—Iyabo S Alli
(74) *Attorney, Agent, or Firm*—Staas & Halsey LLP

(57) ABSTRACT

A wafer measurement/inspection instrument receives information on at least one of a processing result and an operating state of at least one of a coater/developer that performs film forming/resist processing to a wafer and an exposure apparatus that performs liquid immersion exposure to the wafer, and optimizes inspection conditions of the wafer based on the received information (steps 501 and 517). With this operation, quality inspection of the wafer can be efficiently performed, and as a consequence, it becomes possible to efficiently perform processing to the wafer.

69 Claims, 21 Drawing Sheets

SUBSTRATE PROCESSING METHOD, SUBSTRATE PROCESSING SYSTEM, PROGRAM, AND RECORDING MEDIUM

CROSS-REFERENCE TO RELATED APPLICATIONS

This application is a continuation of International Application PCT/JP2007/051555, with an international filing date of Jan. 31, 2007, the disclosure of which is hereby incorporated herein by reference in its entirety, which was not published in English.

BACKGROUND OF THE INVENTION

1. Field of the Invention

The present invention relates to substrate processing methods, substrate processing systems, programs, and recording media, and more particularly, to a substrate processing method and a substrate processing system that performs a plurality of processing to a substrate using a plurality of processing apparatuses, and a program used in the substrate processing system, and a recording medium in which the program is recorded.

2. Description of the Background Art

In an exposure apparatus used in a lithography process for manufacturing electronic devices such as semiconductor devices, an exposure apparatus that exposes a substrate via liquid (hereinafter, also referred to as a "liquid immersion exposure apparatus") has been proposed, in order to improve the resolution by substantially shortening the exposure wavelength, and substantially widen a depth of focus (e.g. refer to the pamphlet of International Publication No. 2004/053955).

In such liquid immersion expose apparatus, when bubbles, dust, contamination (impurities), and the like are generated in liquid used in liquid immersion exposure, there is a possibility that a pattern image, which is formed on a substrate such as a wafer (hereinafter, referred to as a "wafer") by exposure, is deteriorated. Therefore, also in conventional methods, necessary measures were taken in which a wafer after exposure processing is inspected and liquid immersion conditions are changed in accordance with its inspection result, and the like. However, in this case, the measures were taken after abnormality occurred, which could reduce the yield and the like, and therefore they were not always adequate measures.

Further, in the conventional methods, film forming states of various types of films such as a resist film and a topcoat film formed on the wafer are respectively inspected, and when abnormality is recognized, film forming conditions of the respective film forming apparatuses are changed, and the like. However, in such a case, only management of each film is performed, and, for example, the influence that a film forming state of a plurality of films such as a resist film and a topcoat film and the film forming conditions of these films give over the liquid immersion exposure result, and the like have never been considered.

SUMMARY OF THE INVENTION

The present invention has been made under the circumstances described above, and according to a first aspect of the present invention, there is provided a first substrate processing method of performing a plurality of processing to a substrate using a plurality of processing apparatuses, and inspecting quality of the substrate using at least one inspection device, the method comprising: an optimization process of sending information on at least one of a processing result of at least one processing apparatus of the plurality of processing apparatuses and an operating state of the at least one processing apparatus to the at least one inspection device, and optimizing an inspection condition in the at least one inspection device based on the information sent.

With this method, information on at least one of a processing result of at least one processing apparatus among a plurality of processing apparatuses and an operating state of the at least one processing apparatus is sent to at least one inspection device. Then, based on the sent information, inspection conditions in at least one inspection device is optimized. Therefore, efficient quality inspection of the substrate can be performed. Accordingly, it becomes possible to efficiently perform the processing to the substrate as a consequence.

According to a second aspect of the present invention, there is provided a second substrate processing method of performing a plurality of processing to a substrate using a plurality of processing apparatuses that include a liquid immersion exposure apparatus that performs liquid immersion exposure to the substrate and a liquid/foreign material removal device that is arranged on at least one of an inside and an outside of the liquid immersion exposure apparatus and removes at least one of liquid and a foreign material on the substrate, and inspecting quality of the substrate using at least one inspection device, the method comprising: a process of judging whether or not there is a possibility that at least one of liquid and a foreign material on the substrate adversely affects the substrate, based on a result obtained by inspecting a removal processing result of the liquid and the foreign material by the inspection device; a process of sending result information of the judgment to the liquid/foreign material removal device; and a process of performing removal processing of at least one of the liquid and the foreign material again in accordance with the result information of the judgment sent, when a result of the judgment shows that there is a possibility that at least one of the liquid and the foreign material on the substrate adversely affects the substrate.

With this method, the judgment is made of whether or not there is a possibility that at least one of liquid and a foreign material on a substrate adversely affects the substrate based on a result obtained by inspecting a removal processing result of the liquid and the foreign material in the inspection device, and result information of the judgment is sent to the liquid/foreign material removal device. Then, in the case when a result of the judgment shows that there is a possibility that at least one of the liquid and the foreign material on the substrate adversely affects the substrate, removal processing of at least one of the liquid and the foreign material is performed again according to the result information of the judgment that has been sent. In this case, the yield of the products can ultimately be improved. Accordingly, it becomes possible to efficiently perform the processing to the substrate as a consequence.

According to a third aspect of the present invention, there is provided a third substrate processing method of performing a plurality of processing to a substrate using a plurality of processing apparatuses that include a liquid immersion exposure apparatus that performs liquid immersion exposure to the substrate and a liquid/foreign material removal device that is arranged on at least one of an inside and an outside of the liquid immersion exposure apparatus and removes at least one of liquid and a foreign material on the substrate, and inspecting quality of the substrate using at least one inspection device, the method comprising: a process of judging whether or not there is a possibility that at least one of liquid and a foreign material on the substrate adversely affects the substrate, based on a result obtained by inspecting a removal processing result of the liquid and the foreign material by the inspection device; and a process of notifying the liquid/foreign material removal device, when a result of the judgment shows that there is a possibility that at least one of the liquid and the foreign material on the substrate adversely affects the substrate.

With this method, the judgment is made of whether or not there is a possibility that at least one of liquid and a foreign material on the substrate adversely affects the substrate based on a result obtained by inspecting a removal processing result of the liquid and the foreign material in the inspection device. Then, in the case when a result of the judgment shows that there is a possibility that at least one of the liquid and the foreign material on the substrate adversely affects the substrate, the possibility is notified to the liquid/foreign material removal device. In this case, processing conditions can be adjusted in the liquid/foreign material removal device. In this case, processing conditions can be adjusted in the liquid/foreign material removal device. Accordingly, it becomes possible to efficiently perform the processing to the substrate as a consequence.

According to a fourth aspect of the present invention, there is provided a first substrate processing system, comprising: a plurality of processing apparatuses that respectively perform a plurality of processing to a substrate; and at least one inspection device that inspects quality of the substrate, wherein the at least one inspection device receives information on at least one of a processing result of at least one processing apparatus of the plurality of processing apparatuses and an operating state of the at least one processing apparatus, and optimizes an inspection condition based on the information received.

With this system, at least one inspection device receives information on at least one of a processing result of at least one processing apparatus among a plurality of processing apparatuses and an operating state of the at least one processing apparatus. Then, based on the received information, inspection conditions are optimized. Therefore, efficient quality inspection of the substrate can be performed. Accordingly, it becomes possible to efficiently perform the processing to the substrate as a consequence.

According to a fifth aspect of the present invention, there is provided a second substrate processing system, comprising: a liquid immersion exposure apparatus that performs liquid immersion exposure to a substrate; a liquid/foreign material removal device that is arranged on at least one of an inside and an outside of the liquid immersion exposure apparatus and removes at least one of liquid and a foreign material on the substrate to which the liquid immersion exposure has been performed; an inspection device that inspects the substrate to which removal processing of at least one of liquid and a foreign material has been performed by the liquid/foreign material removal device; and a judgment device that judges whether or not there is a possibility that at least one of liquid and a foreign material on the substrate adversely affects the substrate based on an inspection result of the inspection device, and sends result information of the judgment to the liquid/foreign material removal device, wherein when there is a possibility that at least one of the liquid and the foreign material on the substrate adversely affects the substrate, the liquid/foreign material removal device performs removal processing of at least one of the liquid and the foreign material again in accordance with the result information of the judgment sent.

With this system, the judgment device judges whether or not there is a possibility that at least one of liquid and a foreign material on the substrate adversely affects the substrate based on the inspection result of the inspection device, and result information of the judgment is sent to the liquid/foreign material removal device. Then, in the case when there is a possibility that at least one of the liquid and the foreign material on the substrate adversely affects the substrate, the liquid/foreign material removal device performs removal processing of at least one of the liquid and the foreign material again according to the result information of the judgment that has been sent. In this case, the yield of products can be improved ultimately. Accordingly, it becomes possible to efficiently perform the processing to the substrate as a consequence.

According to a sixth aspect of the present invention, there is provided a third substrate processing system, comprising: a liquid immersion exposure apparatus that performs liquid immersion exposure to a substrate; a liquid/foreign material removal device that is arranged on at least one of an inside and an outside of the liquid immersion exposure apparatus and removes at least one of liquid and a foreign material on the substrate to which the liquid immersion exposure has been performed; an inspection device that inspects the substrate to which removal processing of at least one of liquid and a foreign material has been performed by the liquid/foreign material removal device; and a judgment device that judges whether or not there is a possibility that at least one of liquid and a foreign material on the substrate adversely affects the substrate based on an inspection result of the inspection device, and notifies the liquid/foreign material removal device when a result of the judgment shows that there is a possibility that at least one of the liquid and the foreign material on the substrate adversely affects the substrate.

With this system, the judgment device judges whether or not there is a possibility that at least one of liquid and a foreign material on the substrate adversely affects the substrate based on an inspection result of the inspection device. Then, in the case when a result of the judgment shows that there is a possibility that at least one of the liquid and the foreign material on the substrate adversely affects the substrate, the possibility is notified to the liquid/foreign material removal device. In this case, processing conditions can be adjusted in the liquid/foreign material removal device. Accordingly, it becomes possible to efficiently perform the processing to the substrate as a consequence.

According to a seventh aspect of the present invention, there is provided a first program used in a substrate processing system that comprises a plurality of processing apparatuses that respectively perform a plurality of processing to a substrate, and at least one inspection device that inspects quality of the substrate, the program making a computer of the substrate processing system execute: an optimization procedure of sending information on at least one of a processing result of at least one processing apparatus of the plurality of processing apparatuses and an operating state of the at least one processing apparatus to the at least one inspection device, and optimizing an inspection condition in the at least one inspection device based on the information sent.

With this program, the computer of the substrate processing system can be made to execute the first substrate processing method of the present invention, and thus it becomes possible to efficiently perform the processing to the substrate.

According to an eighth aspect of the present invention, there is provided a second program used in a substrate processing system that comprises a plurality of processing apparatuses that include a liquid immersion exposure apparatus that performs liquid immersion exposure to a substrate and a liquid/foreign material removal device that is arranged on at least one of an inside and an outside of the liquid immersion exposure apparatus and removes at least one of liquid and a foreign material on the substrate, and at least one inspection device that inspects quality of the substrate, the program making a computer of the substrate processing system execute: a procedure of judging whether or not there is a possibility that at least one of liquid and a foreign material on the substrate adversely affects the substrate, based on a result obtained by inspecting a removal processing result of the liquid and the foreign material by the inspection device; a procedure of sending result information of the judgment to the liquid/foreign material removal device; and a procedure of performing removal processing of at least one of the liquid and the foreign material again in accordance with the result information of the judgment sent, when a result of the judgment shows that there is a possibility that at least one of the liquid and the foreign material on the substrate adversely affects the substrate.

With this program, the computer of the substrate processing system can be made to execute a second substrate processing method of the present invention, and thus it becomes possible to efficiently perform the processing to the substrate.

According to a ninth aspect of the present invention, there is provided a third program used in a substrate processing system that comprises a plurality of processing apparatuses that include a liquid immersion exposure apparatus that performs liquid immersion exposure to a substrate and a liquid/foreign material removal device that is arranged on at least one of an inside and an outside of the liquid immersion exposure apparatus and removes at least one of liquid and a foreign material on the substrate, and at least one inspection device that inspects quality of the substrate, the program making a computer of the substrate processing system execute: a procedure of judging whether or not there is a possibility that at least one of liquid and a foreign material on the substrate adversely affects the substrate, based on a result obtained by inspecting a removal processing result of the liquid and the foreign material by the inspection device; and a procedure of notifying the liquid/foreign material removal device, when a result of the judgment shows that there is a possibility that at least one of the liquid and the foreign material on the substrate adversely affects the substrate.

With this program, the computer of the substrate processing system can be made to execute a third substrate processing method of the present invention, and thus it becomes possible to efficiently perform the processing to the substrate.

According to a tenth aspect of the present invention, there is provided a computer readable recording medium in which either of the first to third programs of the present invention is recorded.

With this recording medium, the computer can be made to execute either of the first to third programs of the present invention, and thus it becomes possible to efficiently perform the processing to the substrate.

According to an eleventh aspect of the present invention, there is provided a measurement/inspection apparatus that inspects quality of a substrate that has been processed by a plurality of processing apparatuses, the apparatus comprising: a receiving section that receives information on at least one of a processing result of at least one processing apparatus of the plurality of processing apparatuses and an operating state of the at least one processing apparatus, whereby an inspection condition is optimized based on the information received.

With this apparatus, the receiving section receives information on at least one of a processing result of at least one processing apparatus among a plurality of processing apparatuses and an operating state of the at least one processing apparatus. Then, based on the received information, inspection conditions are optimized. Therefore, efficient quality inspection of the substrate can be performed.

BRIEF DESCRIPTION OF THE DRAWINGS

In the accompanying drawings.

DESCRIPTION OF THE EMBODIMENTS

Figure 1:
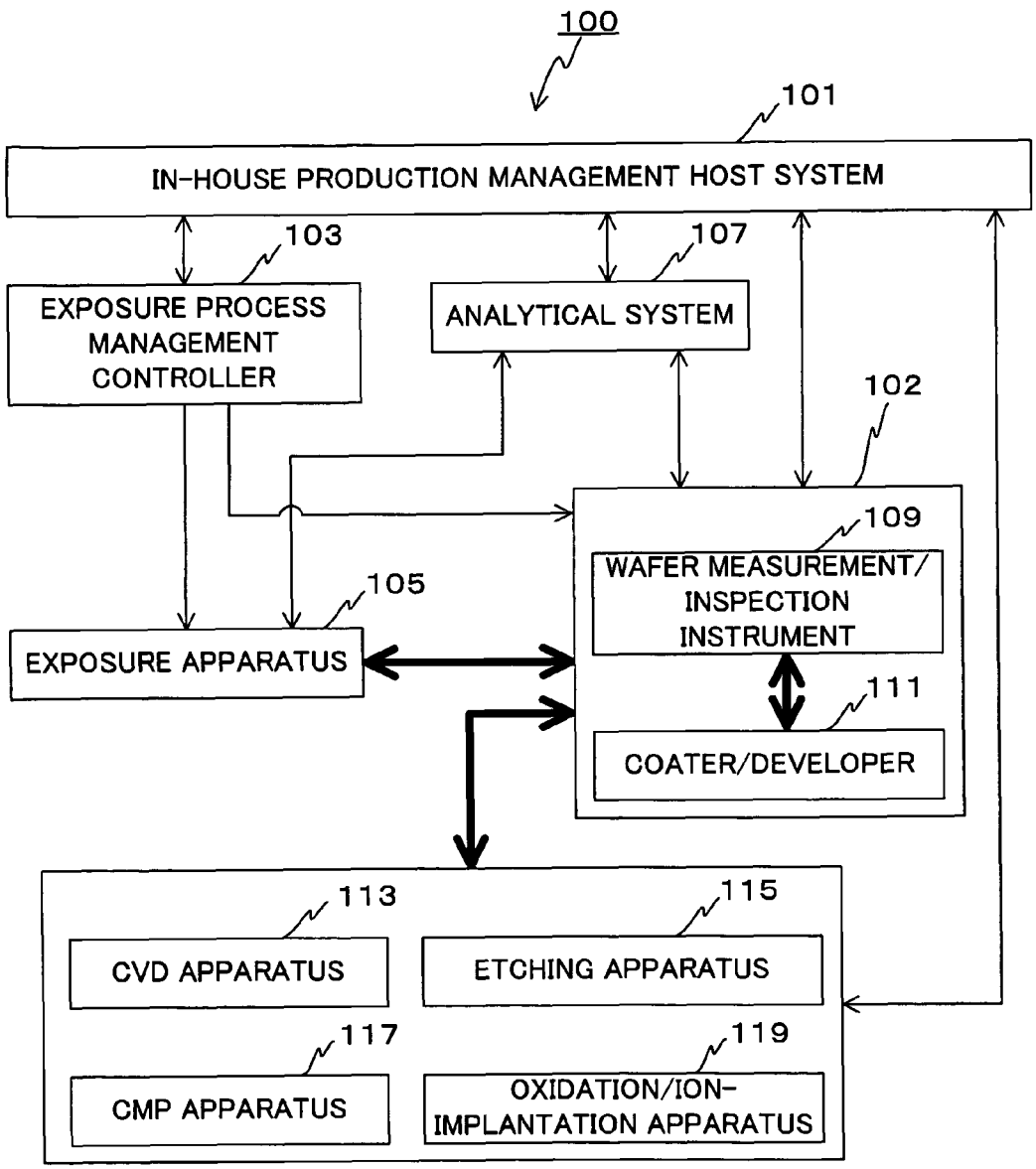
FIG. 1 is a view showing a schematic configuration of a semiconductor manufacturing system related to an embodiment of the present invention.

An embodiment of the present invention will be described below, referring to FIGS. 1 to 24. FIG. 1 shows a schematic configuration of a semiconductor manufacturing system 100 related to the embodiment.

Semiconductor manufacturing system 100 shown in FIG. 1 has an in-house production management host system 101, a track 102, an exposure process management controller 103, an exposure apparatus 105, an analytical system 107, a CVD apparatus 113, an etching apparatus 115, a CMP apparatus 117, an oxidation/ion-implantation apparatus 119, and the like.

Of these constituents, track 102 is inline connected to exposure apparatus 105 via an inline interface (not shown) having a wafer carrier system inside. Inside track 102, a wafer measurement/inspection instrument 109, a coater/developer 111, and the like are installed. And, the constituents above are connected to one another via a duplex communication channel, and transmission/reception of information can be performed. Incidentally, in FIG. 1, two-headed arrows in a thin line indicate a signal and a flow of information, and two-headed arrows in a thick line indicate a flow of a representative signal or information, and a moving route of a wafer. Incidentally, they do not show all the connection relations between the respective blocks.

The processing subject in semiconductor manufacturing system 100 is a semiconductor wafer W (hereinafter, shortly referred to as a "wafer W" as needed) for manufacturing semiconductors.

CVD apparatus 113 supplies one type or a few types of compound gas and single gas, which is composed of element(s) constituting thin film materials, onto wafer W and forms a desired thin film on wafer W by chemical reaction at gas phase or the wafer W surface.

Etching apparatus 115 etches a necessary thickness of an entire surface or a specific area of the thin film formed on wafer W or the wafer W surface.

CMP apparatus 117 planarizes wafer W by chemical mechanical polishing.

Oxidation/ion-implantation apparatus 119 has an oxidation device that forms an oxide film on the surface of wafer W, and an ion-implantation device that implants desired ion to wafer W.

Exposure apparatus 105 performs exposure processing to wafer W. The details of exposure apparatus 105 will be described later.

Exposure process management controller 103 controls exposure apparatus 105 to perform management of an exposure process.

Coater/developer 111 has a coating device that coats a photosensitive agent (photoresist) or the like to wafer W, a development device that develops wafer W to which the exposure processing has been performed, a baking device that bakes wafer W, a measurement device that measures a film forming state and the like, a controller that controls the respective devices, a flash memory in which various programs to be used in the controller are stored, a working memory, and the like.

Wafer measurement/inspection instrument 109 has an inspection device that performs defect inspection, appearance inspection and the like of exposed patterns, a measurement device that performs overlay measurement, linewidth measurement and the like of exposed patterns, a controller that controls the respective devices and also performs optimization of inspection conditions and the like (to be described later). This controller has a flash memory in which various programs to be used in the controller are stored and a working memory.

Analytical system 107 has an analytical device that analyzes information from exposure apparatus 105, information from wafer measurement/inspection instrument 109, and the like. This analytical device has a flash memory in which various programs to be used in the analytical device are stored and a working memory.

In-house production management host system 101 controls the entire semiconductor manufacturing system 100.

Next, exposure apparatus 105 will be explained.

Figure 2:
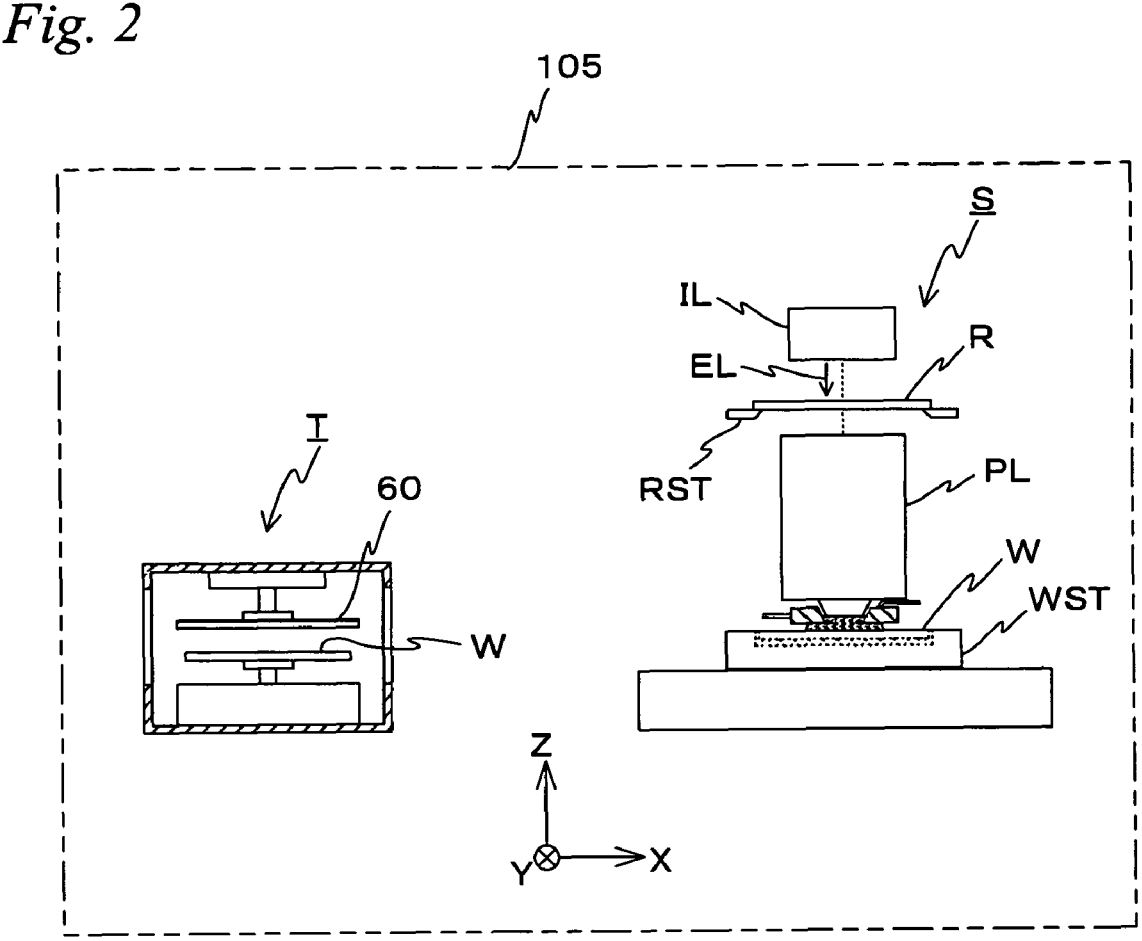
FIG. 2 is a view used to explain an exposure apparatus in FIG. 1.

As shown in FIG. 2 as an example, exposure apparatus 105 is equipped with an exposure apparatus main section S that performs exposure processing to wafer W, a removal device T that removes liquid, a foreign material or the like adhering on wafer W, and the like. In this case, a predetermined direction within a horizontal plane is to be an X-axis direction, a direction orthogonal to the X-axis direction within the horizontal plane is to be a Y-axis direction, and a direction orthogonal to the X-axis direction and the Y-axis direction respectively is to be a Z-axis direction. Further, rotational (tilt) directions around an X-axis, a Y-axis, and a Z-axis are to be a θX direction, a θY direction, and a θZ direction, respectively.

Figure 3:
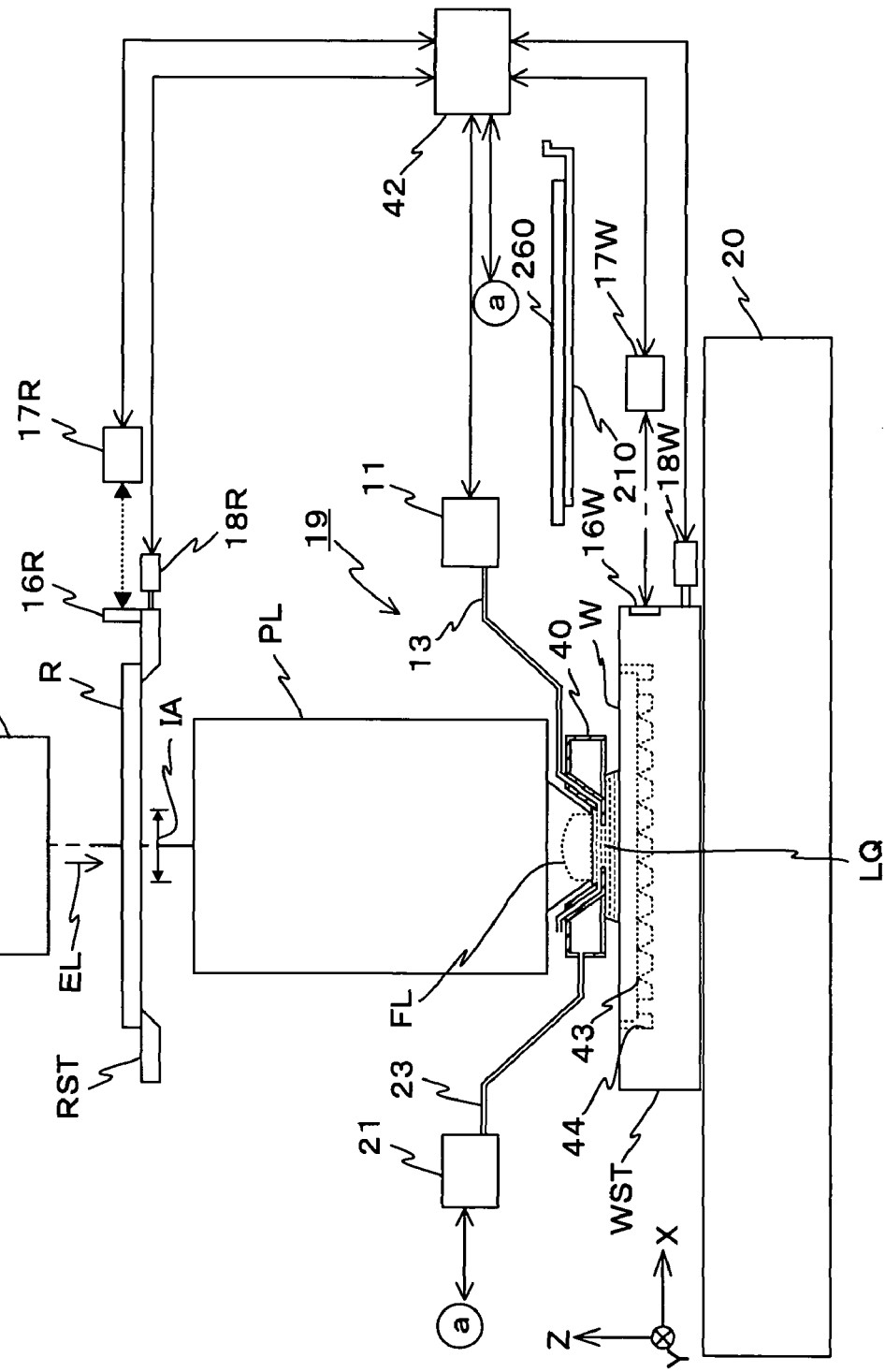
FIG. 3 is a view used to explain an exposure apparatus main section in FIG. 2.

As shown in FIG. 3 as an example, exposure apparatus main section S in the embodiment is a liquid immersion exposure apparatus that exposes wafer W via liquid in order to improve the resolution by substantially shortening the exposure wavelength and also to substantially increase the depth of focus.

Exposure apparatus main section S shown in FIG. 3 is equipped with a reticle stage RST that holds a reticle R, a reticle stage drive device 18R that drives reticle stage RST, a laser interferometer 17R that measures the position of reticle stage RST, a wafer stage WST that holds wafer W, a wafer stage drive device 18W that drives wafer stage WST, a laser interferometer 17W that measures the position of wafer stage WST, an illumination system IL that illuminates reticle R held y reticle stage RST with an exposure light EL, a projection optical system PL that projects a pattern image of reticle R illuminated by exposure light EL on wafer W, a base member 20 on which wafer stage WST is mounted, a liquid immersion system 19, a liquid immersion monitor device 260, and a main controller 42 that controls the respective components of exposure apparatus main section S. Main controller 42 has a flash memory (omitted in the drawing) in which various programs to be used in main controller 42 are stored, a working memory (omitted in the drawing), and the like.

Illumination system IL illuminates a predetermined illumination area IA of reticle R with exposure light EL having a uniform illuminance distribution. As exposure light EL, for example, a deep ultraviolet light (DUV light) such as an emission line (g-line, h-line, i-line) emitted from a mercury lamp and a KrF excimer laser light (wavelength: 248 nm), a vacuum ultraviolet light (VUV light) such as an ArF excimer laser light (wavelength: 193 nm) and an $F_2$ laser light wavelength: 157 nm), or the like is used. In the embodiment, an ArF excimer laser light is to be used as an example.

Reticle stage drive device 18R includes an actuator such as a linear motor, and drives reticle stage RST in the X-axis direction, the Y-axis direction, and the θz direction.

Laser interferometer 17R measures the position of reticle stage RST by emitting a laser light toward a movable mirror 16R arranged on reticle stage RST, and receiving a reflected light from movable mirror 16R. The measurement result of laser interferometer 17R is notified to main controller 42. Main controller 42 drives reticle stage drive device 18R based on the measurement result of laser interferometer 17R, and performs position control of reticle R held by reticle stage RST.

Projection optical system PL has a plurality of optical elements held in a barrel, and projects a pattern image of reticle R to wafer W at a predetermined magnification.

Projection optical system PL of the embodiment is a reduction system whose projection magnification is ¼, ⅕, ⅛ or the like. Incidentally, projection optical system PL may be any one of an equal magnifying system and a magnifying system. Further, projection optical system PL may be any one of a dioptric system that does not include catoptric elements, a catoptric system that does not include dioptric elements, and a catadioptric system that includes catoptric elements and dioptric elements. Furthermore, projection optical system PL may form any one of an inverted image and an upright image.

Wafer stage WST has a holder 43 that holds wafer W and liquid immersion monitor device 260 by vacuum suction. Holder 43 is placed on the bottom surface of a recessed section 44 formed on the surface of wafer stage WST on the +Z side.

Wafer stage drive device 18W includes an actuator such as a linear motor, and drives wafer stage WST on base member 20 in the X-axis, Y-axis, Z-axis, θX, θY, and θZ directions.

Laser interferometer 17W measures the position of wafer stage WST by emitting a laser light toward a movable mirror 16W arranged on wafer stage WST, and receiving a reflected light from movable mirror 16W. The measurement result of laser interferometer 17W is notified to main controller 42. Further, positional information of wafer W held by holder 43 in the Z-axis, θX, and θY directions is detected by a focus-leveling detection system (not shown) and the detection result is notified to main controller 42. Main controller 42 drives wafer stage drive device 18W based on the measurement result of laser interferometer 17W and the detection result of the focus-leveling detection system, and performs position control of wafer W held by holder 43.

<<Liquid Immersion System>>

Liquid immersion system 19 forms an area (hereinafter, also referred to as a "liquid immersion area") that is filled with liquid LQ between projection optical system PL and wafer W. In this case, as shown in FIG. 3 as an example, liquid immersion system 19 is equipped with a nozzle member 40, a supply pipe 13, a light source for illumination 15 (omitted in FIG. 3, refer to FIG. 4), a recovery pipe 23, a liquid supply device 11, a liquid recovery device 21 and the like.

Figure 4:
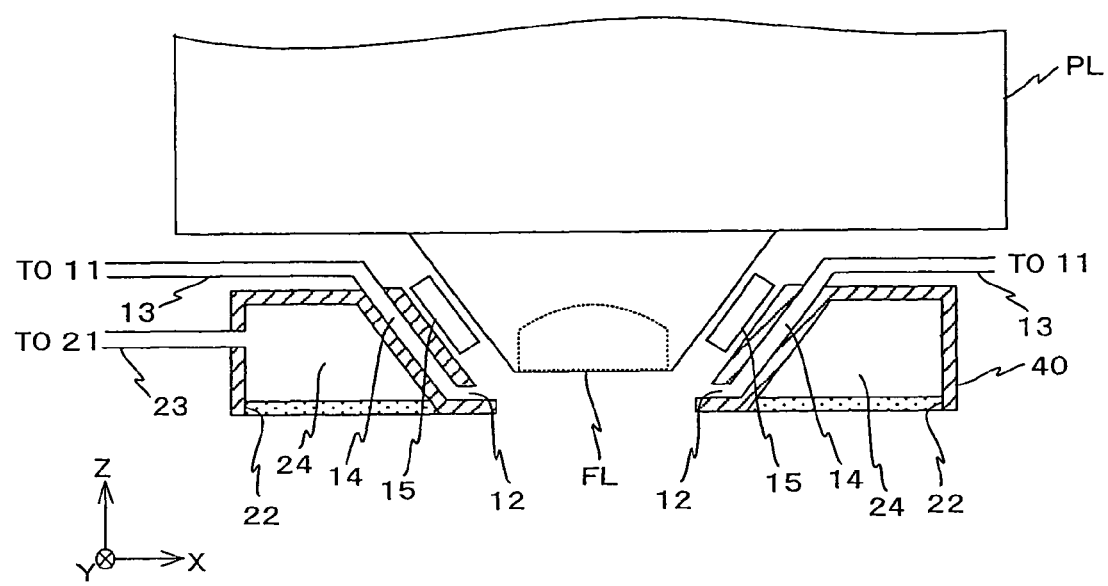
FIG. 4 is a view used to explain a liquid immersion system in FIG. 3.

Nozzle member 40 is an annular member that is arranged so as to enclose an optical element FL that is closest to an image plane of projection optical system PL out of a plurality of optical elements of projection optical system PL, and as shown in FIG. 4 as an example, nozzle member 40 has a supply opening 12 used to form the liquid immersion area by supplying liquid LQ in the space between wafer W held by holder 34 and optical element FL, and a recovery opening 22 used to recover liquid LQ in the liquid immersion area. At recovery opening 22, for example, a mesh member made of titanium or a porous member made of ceramic is placed. Further, inside nozzle member 40, a flow channel 14 that connects supply opening 12 and one end of supply pipe 13, and a flow channel 24 that connects recovery opening 22 and one end of recovery pipe 23. Incidentally, in the embodiment, pure water is used as liquid LQ as an example.

Accordingly, in the embodiment, out of a plurality of optical elements of projection optical system PL, only optical element FL that is closest to the image plane of projection optical system PL comes into contact with liquid LQ.

Light source for illumination 15 is installed on the periphery of the liquid immersion area, and illuminates the vicinity of the liquid immersion area and optical element FL while liquid immersion monitor device 260 is operating.

Liquid supply device 11 is connected to the other end of supply pipe 13. Liquid supply device 11 has a temperature adjusting device that adjusts the temperature of liquid LQ to be supplied and a degassing device that reduces a gas component in liquid LQ to be supplied, a filter unit that removes a foreign material in liquid LQ to be supplied, and the like, and liquid supply device 11 sends out liquid LQ that is clean and its temperature is adjusted. That is, liquid LQ sent out from liquid supply device 11 is supplied to the liquid immersion area via supply pipe 13, flow channel 14, and supply opening 12. Incidentally, liquid supply device 11 is controlled by main controller 42.

Liquid recovery device 21 is connected to the other end of recovery pipe 23. Liquid recovery device 21 has a discharge system including a vacuum device, and recovers liquid LQ. That is, liquid LQ in the liquid immersion area is recovered by liquid recovery device 21 via recovery opening 22, flow channel 24, and recovery pipe 23. Incidentally, liquid recovery device 21 is controlled by main controller 42.

Main controller 42 performs liquid supply by liquid supply device 11 and liquid recovery by liquid recovery device 21 in parallel at least while the exposure processing is being performed.

Figure 5A:
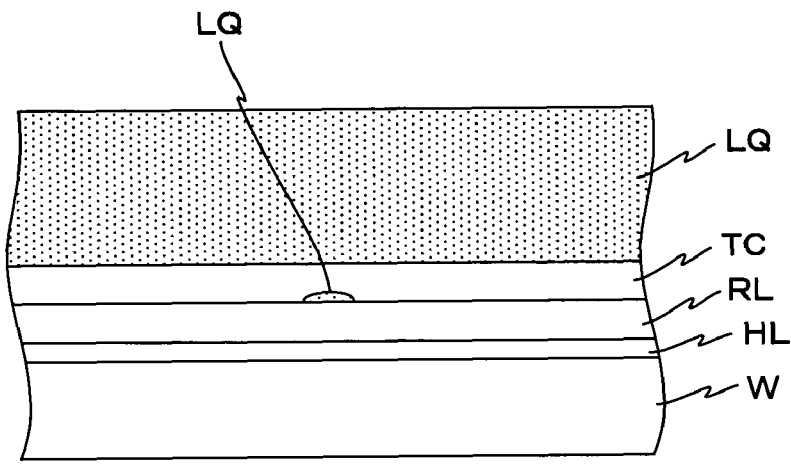
FIGS. 5A to 5C are views each used to explain a problem peculiar to the liquid immersion system.
Figure 5B:
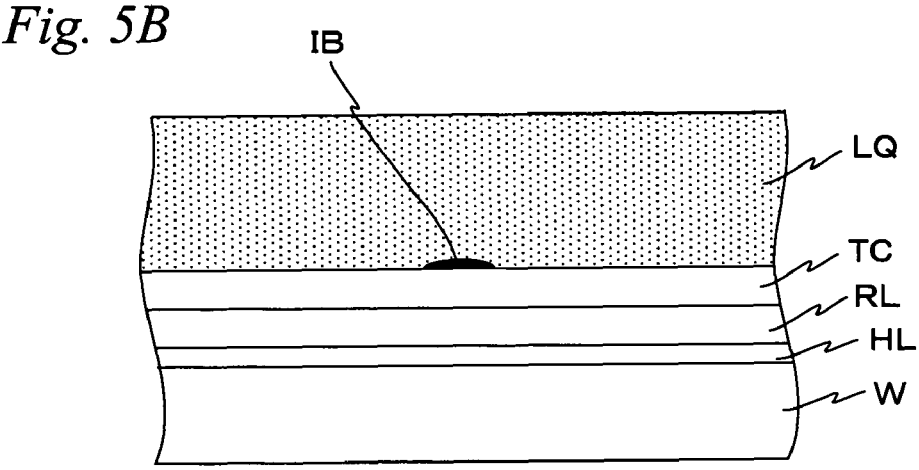
Figure 5C:
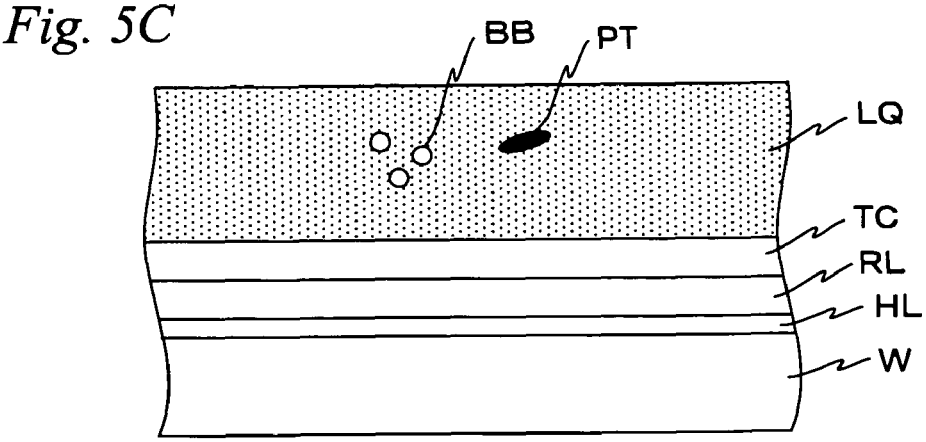

Meanwhile, as shown in FIG. 5A as an example, liquid LQ comes in a boundary portion between resist film RL and topcoat film TC in some cases. In such cases, liquid LQ seeps into the resist and changes the resist performance, which could deteriorate the uniformity of the exposure pattern as a consequence. Further, as shown in FIG. 5B as an example, a foreign material IB such as a particle or a watermark adheres on topcoat film TC in some cases. In such cases, even when exposure is performed normally, the PEB processing and the development processing after exposure are affected, which could generate defect of a pattern formed on a wafer by exposure (hereinafter, shortly referred to an "exposure pattern" as needed) such as breaking of wire, short, or variation in linewidth. Moreover, as shown in FIG. 5C as an example, a foreign material such as bubbles BB or a particle PT exists in the liquid immersion area in some cases. In such cases, the optical path of an exposure light changes, which could generate defect of the exposure pattern. Further, when elution of the resist into liquid LQ occurs, optical element FL is contaminated, which could generate defect of the exposure pattern. Incidentally, there is a possibility that bacteria comes into existence in liquid LQ and at members (such as supply pipe 13, and optical element FL) that contact with liquid LQ, and the bacteria is regarded as one of foreign materials. Further, a reference sign HL in FIGS. 5A to 5C indicates an antireflection film.

<<Liquid Immersion Monitor Device>>

Figure 6A:
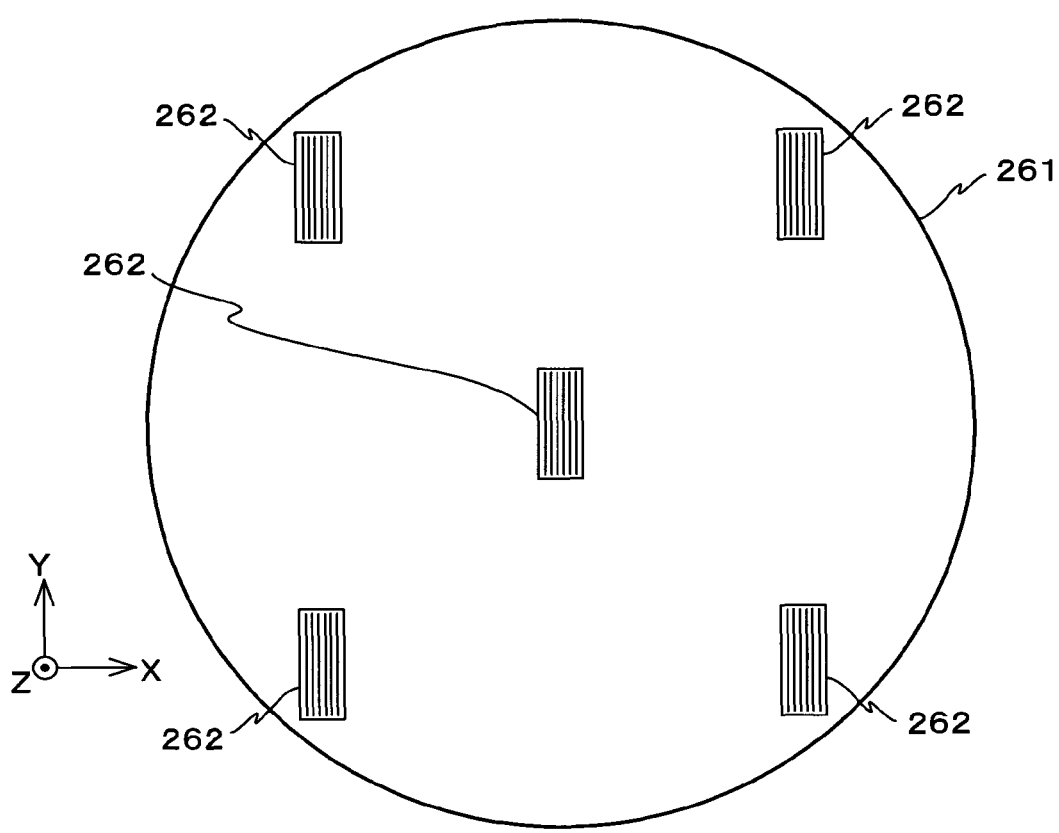
FIGS. 6A and 6B are views each used to explain a liquid immersion monitor device.
Figure 6B:
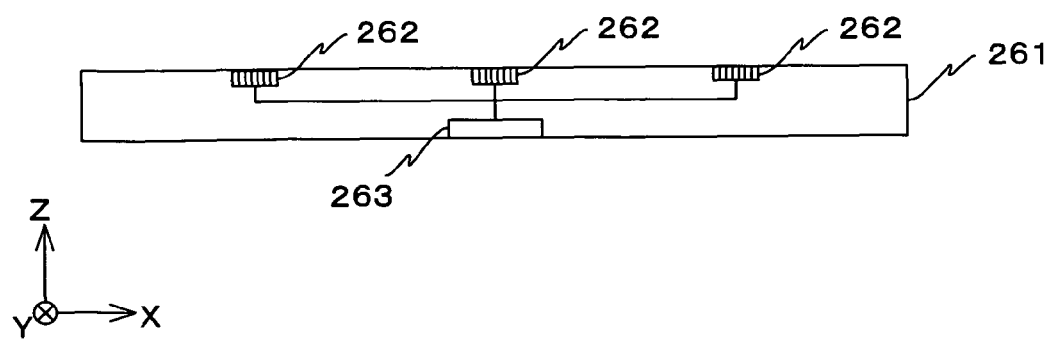

Liquid immersion monitor device 260 is a device that inspects whether or not a foreign material is included in the liquid immersion area, whether or not optical element FL is contaminated, and the like. In this case, as shown in FIGS. 6A and 6B as an example, liquid immersion monitor device 260 has a base material 261 whose outer shape is substantially the same as wafer W, a plurality of CCD sensor modules 262 embedded on base material 261, and an analytical device 263 that analyzes the output signal of each CCD sensor module and wirelessly transmits the analytical result. Analytical device 263 has a flash memory in which various programs to be used in analytical device 263 are stored, a working memory, and the like. In this case, one CCD module 262 is embedded in the center portion of base material 261, and four CCD sensor modules 262 are embedded at substantially an equal distance in the circumferential area of base material 261. Incidentally, the analytical result at analytical device 263 is notified from analytical device 263 to main controller 42, exposure process management controller 103, analytical system 107, and the like.

As materials of base material 261, materials which less affect liquid LQ when coming into contact with liquid LQ can be used. For example, the same material as that of wafer W may be used, or metals such as titanium or materials containing fluorine series resins such as PTFE and PFA may be used. Further, in order to apply water repellency to a surface that contacts with liquid LQ of base material 261, a film having water repellency may be formed on the surface.

Figure 7:
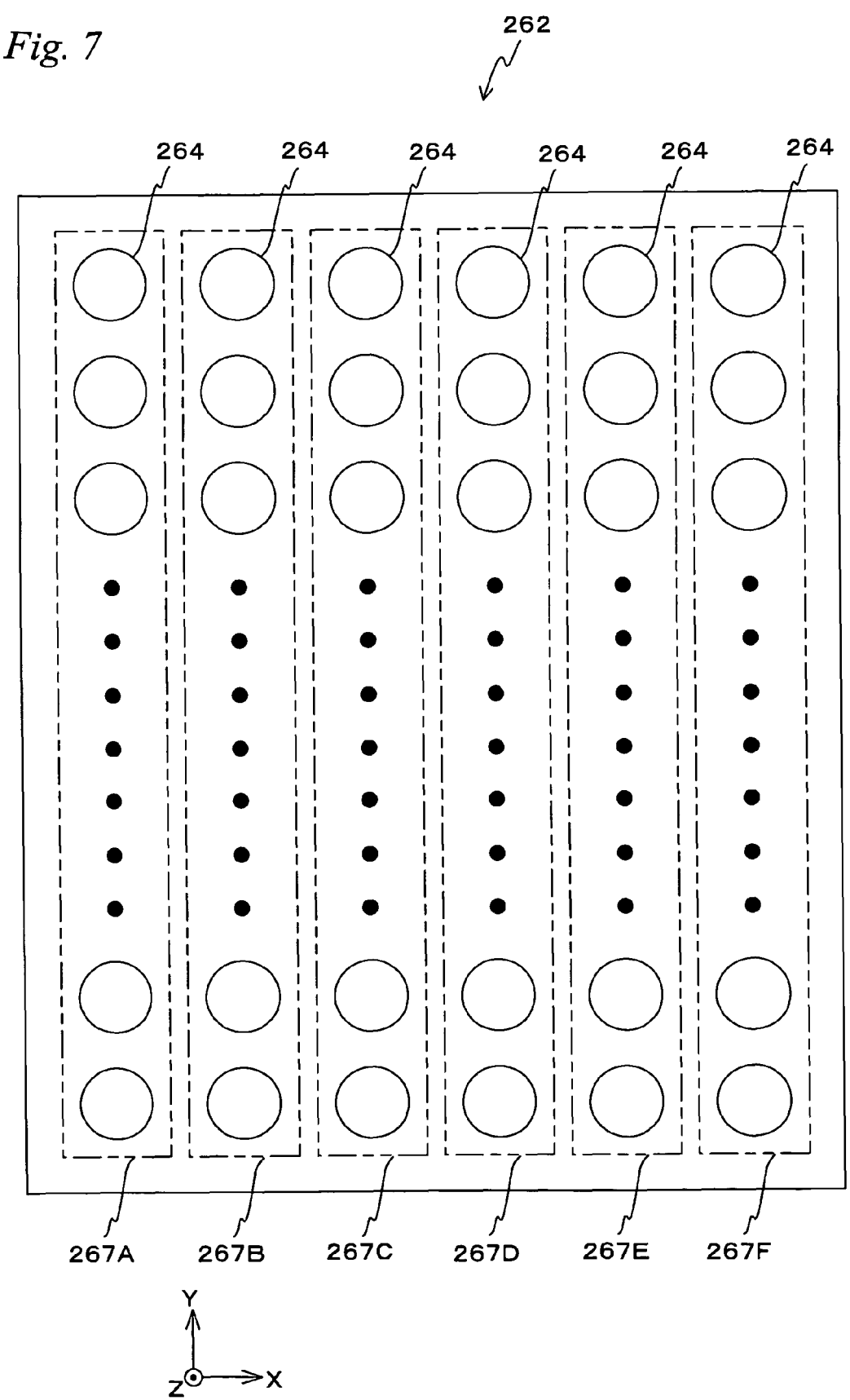
FIG. 7 is a view used to explain a CCD sensor module of the liquid immersion monitor device.

As shown in FIG. 7 as an example, each CCD sensor module 262 has six one-dimensional line sensors having a longitudinal direction in the Y-axis direction. In this case, a one-dimensional line sensor located at the −X-side end portion is to be a line sensor 267A, a one-dimensional line sensor located on the +X-side of line sensor 267A is to be a line sensor 267B, a one-dimensional line sensor located on the +X-side of line sensor 267B is to be a line sensor 267C, a one-dimensional line sensor located on the +X-side of line sensor 267C is to be a line sensor 267D, a one-dimensional line sensor located on the +X-side of line sensor 267D is to be a line sensor 267E, and a one-dimensional line sensor located on the +X-side of line sensor 267E is to be a line sensor 267F. Further, a plurality of microlenses 264 are arranged in each line sensor so as to correspond to photodetection sections of the line sensor.

Figure 8:
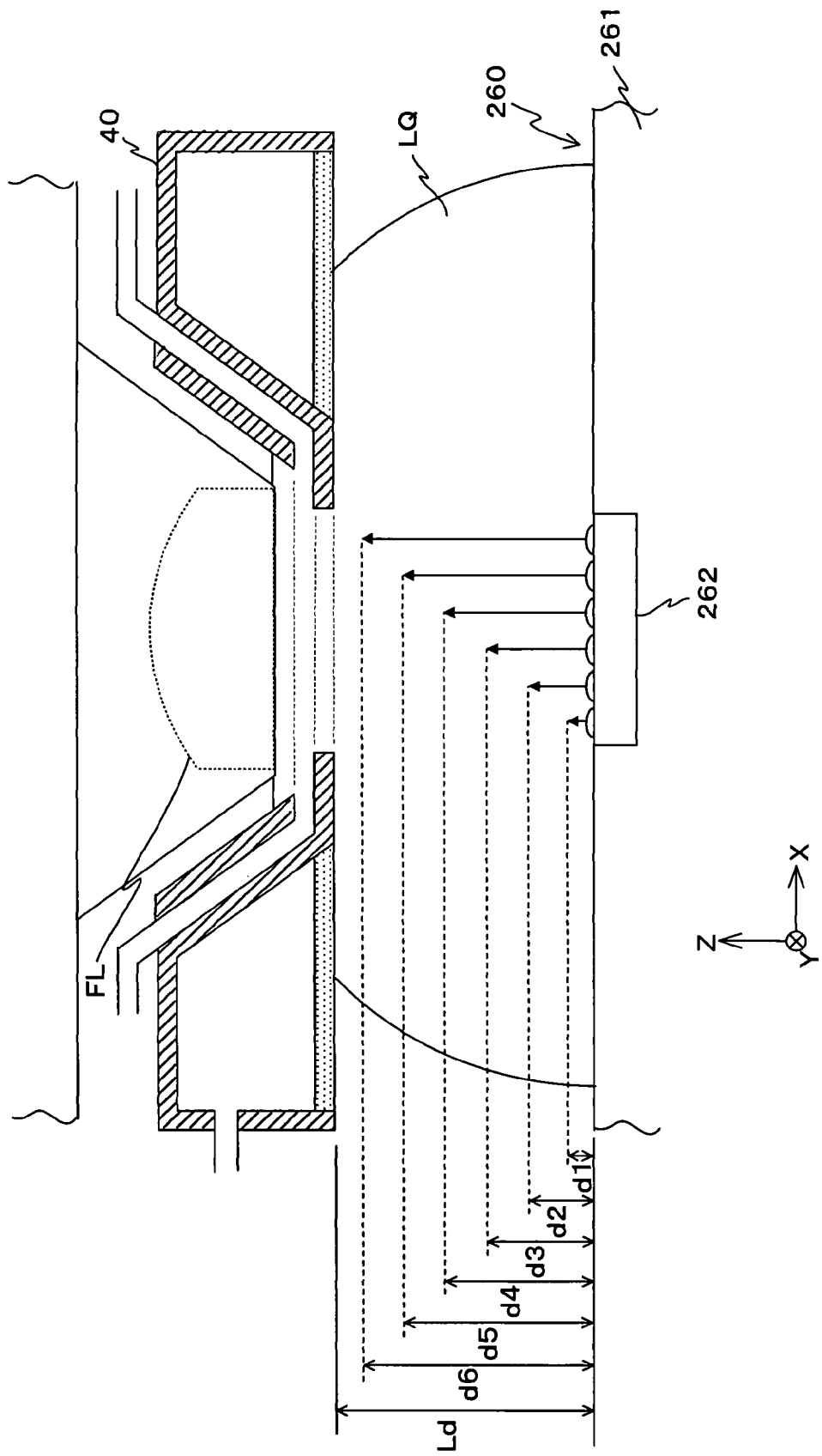
FIG. 8 is a view used to explain an object plane position of each line sensor in the CCD sensor module of FIG. 7.
Figure 9:
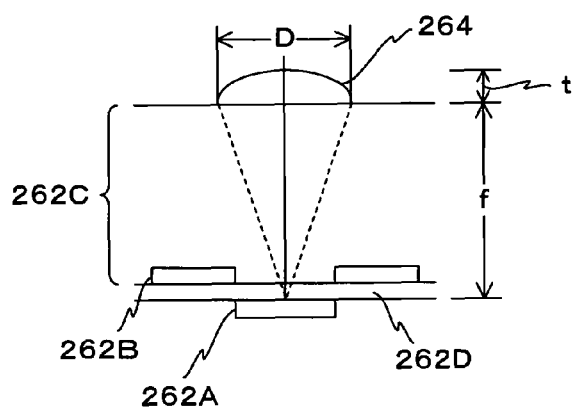
FIG. 9 is a view used to explain the line sensor in FIG. 8.

A focal distance of microlens 264 is different depending on each line sensor. That is, a distance to a position subject to observation (object plane position) of each line sensor is different from each other. Then, an offset amount of the object plane position of each line sensor is set in view of the substantial depth of focus in accordance with the detection resolution of foreign material. In this case, as shown in FIG. 8 as an example, the position subject to observation of line sensor 267A is a position a distance d1 away from the surface of base material 261, the position subject to observation of line sensor 267B is a position a distance d2 (>d1) away from the surface of base material 261, the position subject to observation of line sensor 267C is a position a distance d3 (>d2) away from the surface of base material 261, the position subject to observation of line sensor 267D is a position a distance d4 (>d3) away from the surface of base material 261, the position subject to observation of line sensor 267E is a position a distance d5 (>d4) away from the surface of base material 261, and the position subject to observation of line sensor 267F is a position a distance d6 (>d5) away from the surface of base material 261. Therefore, for example, when the thickness of the liquid immersion area (the length in the X-axis direction) is around 3 mm, almost the entire area of the liquid immersion area can be inspected by setting d1=0.25 mm, d2=0.75 mm, d3=1.25 mm, d4=1.75 mm, d5=2.25 mm, and d6=2.75 m.

For example, assuming that a diameter D of microlens 264 is 8 μm and a focal distance f is 12.0 μm, an F number is 1.5 (=f/D). when a white LED (a wavelength λ: 560 nm) is used as an illumination light source, a depth of focus=±0.61λF/NA=±0.61λF$^2$=±1.54 μm. Incidentally, a center thickness t (refer to FIG. 9) of microlens 264 can be 2 to 3 μm. A reference sign 262A in FIG. 9 indicates a CCD pixel, a reference sign 262B indicates a transfer electrode, a reference sign 262C indicates a resin layer, and a reference sign 262D indicates an insulation film.

Figure 10:
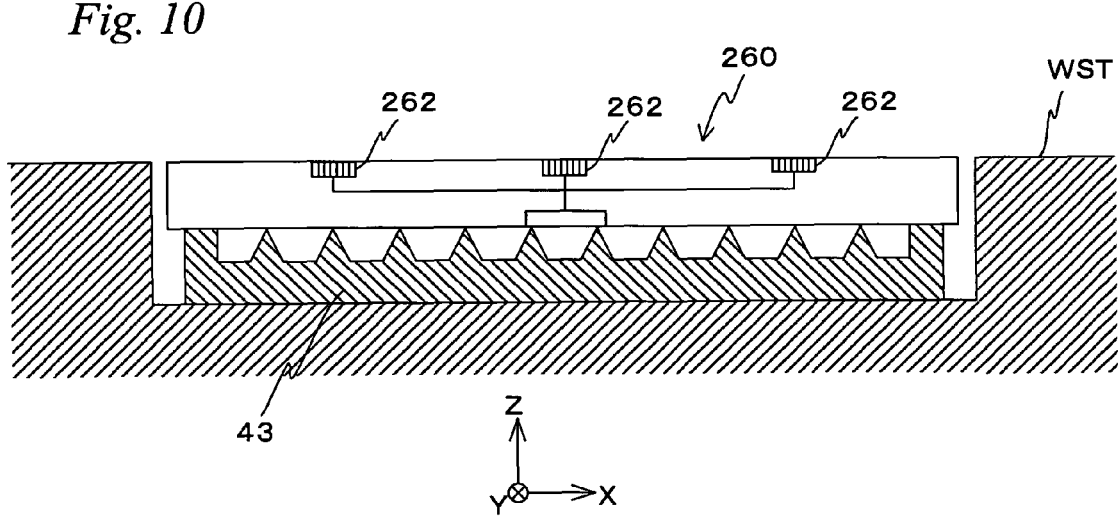
FIG. 10 is a view used explain the liquid immersion monitor device set in a substrate holder.

Liquid immersion monitor device 260 is housed in advance at a predetermined position within exposure apparatus main section S, and when liquid immersion monitoring processing is performed, liquid immersion monitor device 260 is set on holder 43 by a carrier device 210 (refer to FIG. 3) as shown in FIG. 10 as an example.

Meanwhile, as methods of CCD (Charge-Coupled Device), there are an interline method, a frame interline method, a frame transfer method and the like depending on a structure that transfers signal charge, and any of these methods may be used, but the frame transfer method is preferable in which a photodetection area size can be large because the photodetection section also serves as a transfer section.

Further, assuming that a CCD pixel size Cs is 8.0 μm (including a 2.0 μm dead zone), an effective pixel number Cp of the line sensor is 4000 (32 mm length), a CCD scanning data rate Cd is 25 nsec/pixel (=40 MHz), scanning time per line Tc of the line sensor will be Cp×Cd=100 μsec. Then, a stage scanning speed Sp at the time of liquid immersion monitoring will be Cs/Tc=80 mm/sec.

Incidentally, in liquid immersion monitor device 260, each line sensor may be formed on base material 261 using a method of photolithography, or the CCD sensor module created in advance may be pasted on base material 261.

<<Removal Device>>

Figure 11:
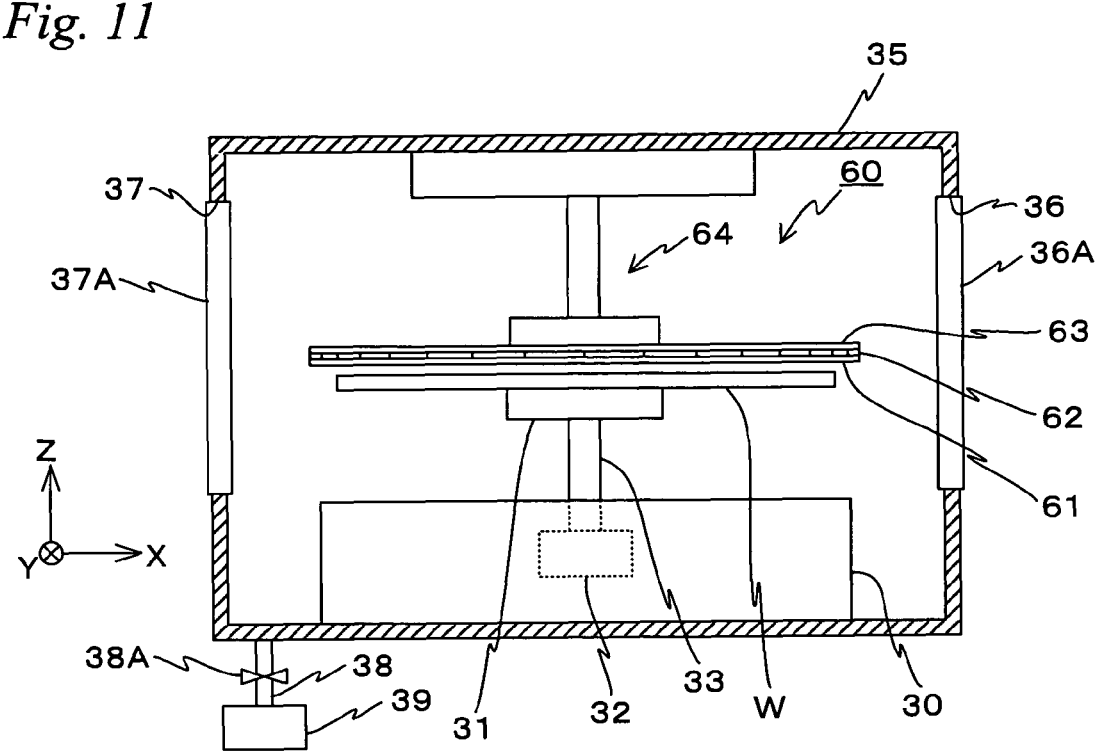
FIG. 11 is a view used to explain a removal device T in FIG. 2.

Removal device T is a device that removes liquid LQ, a foreign material and the like (hereinafter, also described as "liquid/foreign material" for the sake of convenience) adhering on wafer W. In this case, as shown in FIG. 11 as an example, removal device T has a stage device 30, a holder 31 that holds wafer W by vacuum suction, a rotation device 32 that drives and rotates holder 31, a generation device 60 that generates a flexure travelling wave used to move liquid/foreign material adhering on wafer W, a chamber 35, a liquid suction device 39, an observation device (omitted in the drawing) that observes the surface of wafer W, and the like. Stage device 30, holder 31, rotation device 32 and generation device 60 are housed within chamber 35. Incidentally, the observation result of the observation device is notified to main controller 42, wafer measurement/inspection instrument 109, analytical system 107 and the like.

Chamber 35 has an opening section 36 formed on the wall surface on the +X side in FIG. 11 and an opening section 37 formed on the wall surface on the −X side. At opening section 36, a shutter 36A that opens/closes opening section 36 is arranged, and at opening section 37, a shutter 37A that opens/closes opening section 37 is arranged. Wafer W to which liquid immersion exposure has been performed is carried into chamber 35 via opening section 36, and wafer W to which removal processing of liquid/foreign material has been performed is carried to the outside of chamber 35 via opening section 37. The opening/closing of each shutter is controlled by main controller 42.

Liquid suction device 39 is connected to chamber 35 via a flow channel 38 where a valve 38A is arranged. When valve 38A is in an opened state, liquid within chamber 35 is drained to the outside of chamber 35 by liquid suction device 39. Incidentally, during the removal processing of liquid/foreign material, valve 38A is in an opened state.

Rotation device 32 has an axis 33 connected to holder 31, and a motor that is placed inside stage device 30 and drives and rotates axis 33, and rotates wafer W held by holder 31. Incidentally, holder 31 is drivable together with axis 33 in the Z-axis direction, the θX direction and the θY direction by a holder drive device (not shown).

Figure 12:
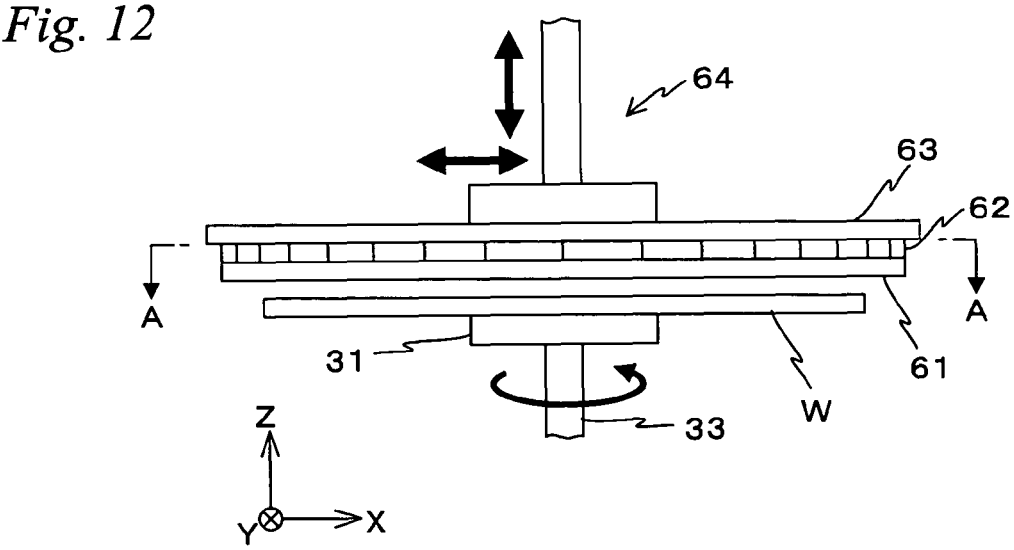
FIG. 12 is a view used to explain a generation device in FIG. 11.

As shown in FIG. 12 as an example, generation device 60 has an elastic stator 61 that is placed facing wafer W held by holder 31 and generates a flexure travelling wave, an oscillating body 62 that is placed on the surface on the +Z side of elastic stator 61 and includes a piezo element that excites the flexure travelling wave, a support member 63 that supports oscillating body 62, and a drive mechanism 64 that drives support member 63 in the X-axis direction, the Y-axis direction, the Z-axis direction, the θX direction, the θY direction, and the θZ direction. Drive mechanism 64 is controlled by main controller 42. That is, a distance between elastic stator 61 and wafer W, and a tilt angle of elastic stator 61 with respect to wafer W, the position of elastic stator 61 with respect to wafer W within the XY plane and the like can be adjusted by main controller 42.

Figure 13:
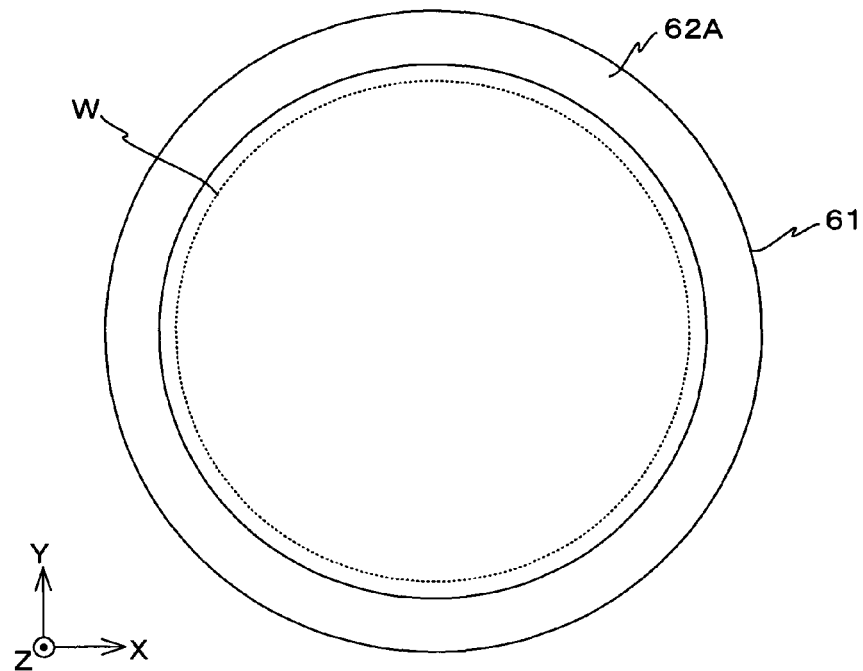
FIG. 13 is a view used to explain an elastic stator and an oscillating body in FIG. 11.

As shown in FIG. 13 as an example, elastic stator 61 is an elastic member having a roughly circular shape that is slightly larger than wafer W. To the surface on the −Z side of elastic stator 61, water repellent coat is applied. Then, on the circumferential area on the surface on the +Z side of elastic stator 61, a piezo element 62A is placed in a ring-shaped arrangement so that a desirable flexure travelling wave can be obtained. Incidentally, elastic stator 61 may also have a ring shape.

Figure 14:
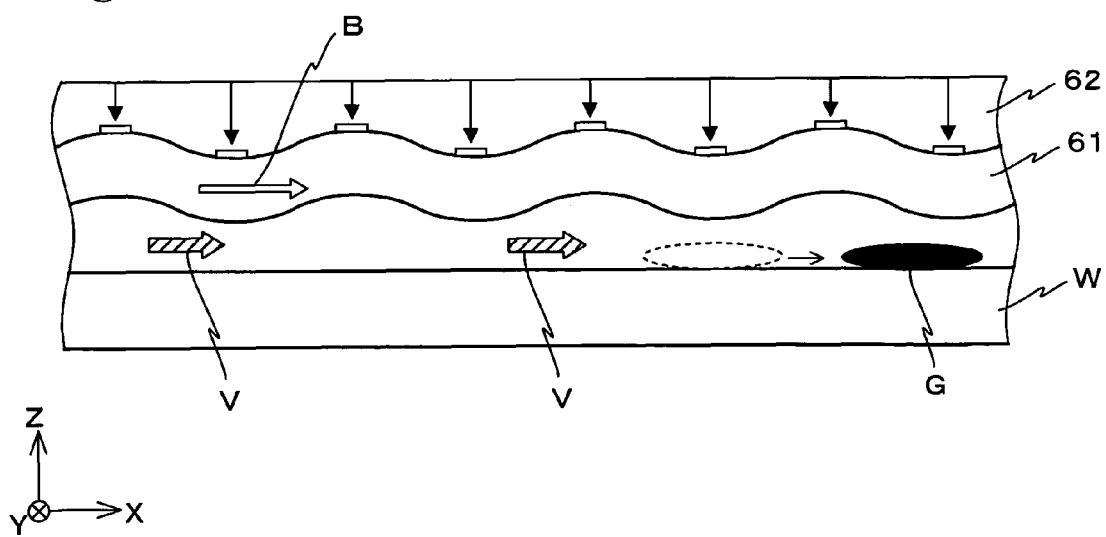
FIG. 14 is a view (No. 1) used to explain an action of the generation device in FIG. 12.
Figure 15:
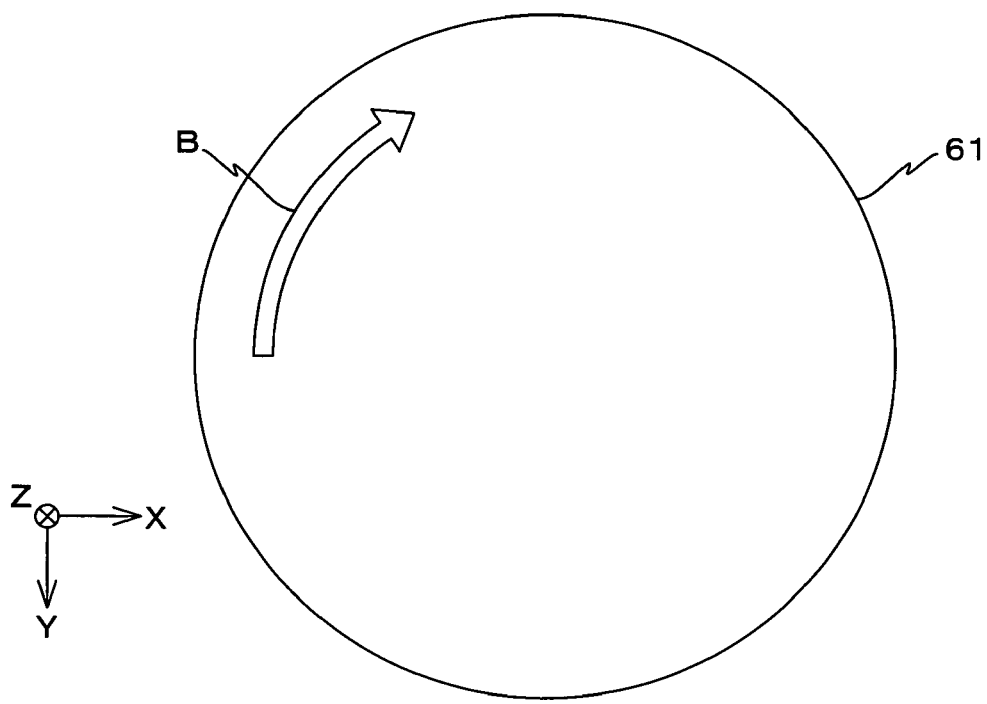
FIG. 15 is a view (No. 2) used to explain an action of the generation device in FIG. 12.

The piezo element of oscillating body 62 is uniformly polarized in a direction of its thickness (in this case, the Z-axis direction), and a plurality of electrodes (hereinafter, also referred to as an "electrode group") having a pitch of half-wavelength of the flexure oscillation are arranged. Then, when the electric signal of a resonant frequency is input to this electrode group, a standing wave of flexure oscillation is excited. Accordingly, as shown in FIG. 14 as an example, a flexure travelling wave B is generated and an acoustical field is generated between elastic stator 61 and wafer W by flexure travelling wave B. Then, due to an acoustical viscous flow V in the acoustical field, liquid/foreign material G adhering on wafer W moves. That is, generation device 60 can move the liquid/foreign material adhering on wafer W in a non-contact state with wafer W. Further, even if a recessed section is formed on the surface of wafer W and liquid/foreign material comes inside the recessed section, the liquid/foreign material coming inside the recessed section can be removed to the outside of the recessed section. In this case, as shown in FIG. 15 as an example, flexure travelling wave B whose travelling direction is in a circumferential direction of elastic stator 61 is generated. Therefore, acoustical viscous flow V flows in the circumferential direction of wafer W as its travelling direction. Incidentally, the electrode group does not have to be arranged on the entire surface of oscillating body 62, but only has to be arranged on the partial surface. In this case, by arranging one more pair of electrode groups and making setting so that the phase difference between standing waves excited by these electrode groups becomes π/2 (=¼ wavelength), oscillation is excited and a flexure travelling wave is generated.

When tilting holder 31 with respect to the XY plane, along with generation of flexure travelling wave B, the synergetic effect of the gravity action and the action by the flexure travelling wave, the liquid/foreign material adhering on wafer W can favorably be removed.

Figure 16:
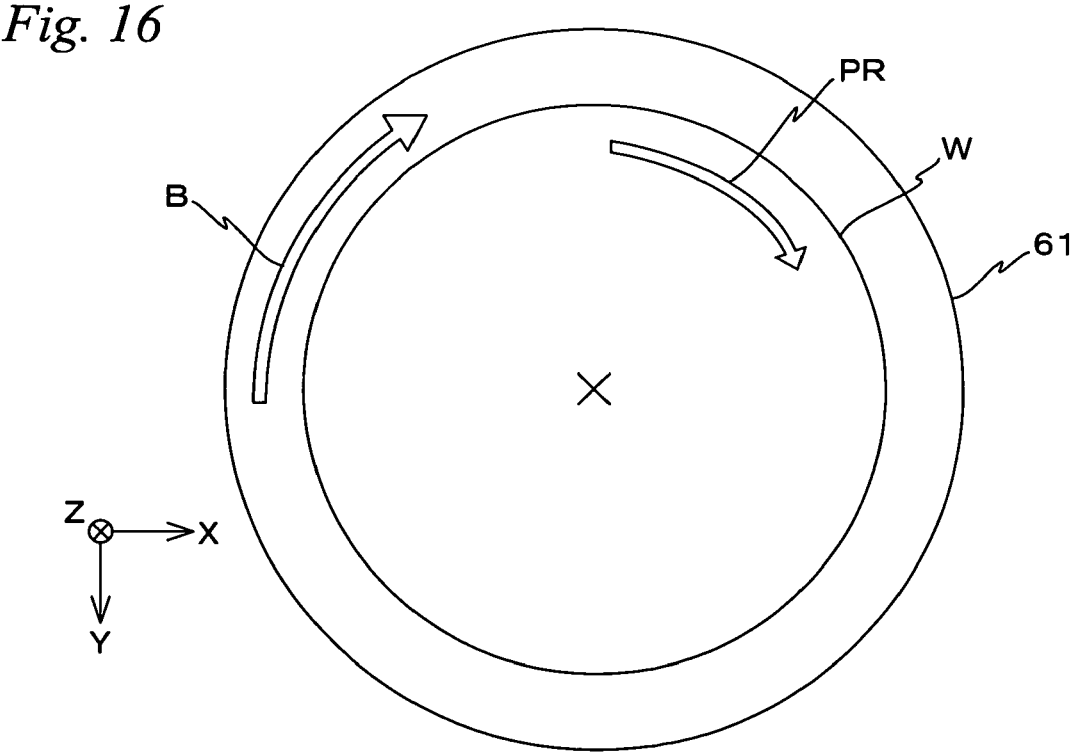
FIG. 16 is a view (No. 3) used to explain an action of the generation device in FIG. 12.

Further, along with generation of flexure travelling wave B, when wafer W is rotated, the centrifugal force is added, and therefore the liquid/foreign material adhering on wafer W can be more favorably moved. In this case, as shown in FIG. 16 as an example, when a rotational direction PR of wafer W is made to coincide with a travelling direction of flexure travelling wave B, a direction of acoustical viscous flow V and a direction of the centrifugal force substantially coincide, and therefore even if wafer W is rotated at a relatively low speed, liquid/foreign material adhering on wafer W can be favorably removed. Accordingly, it becomes possible to decrease the load to wafer W, decrease the power consumption of rotation device 32, suppress the heat generation of rotation device 32, and downsize rotation device 32.

Meanwhile, the generation start of flexure travelling wave B and the rotation start of wafer W may be performed substantially at the same time, or generation of flexure travelling wave B may be started after the rotation of wafer W is started. Further, for example, when liquid/foreign material comes inside the recessed section formed on the surface of wafer W, the rotation of wafer W may be started after a predetermined period of time elapses from the start of generation of flexure travelling wave B. In this case, the liquid/foreign material coming inside the recessed section is first moved to the outside of the recessed section by flexure travelling wave B, and then the liquid/foreign material can be removed from the surface of wafer W by the rotation of wafer W.

Figure 17:
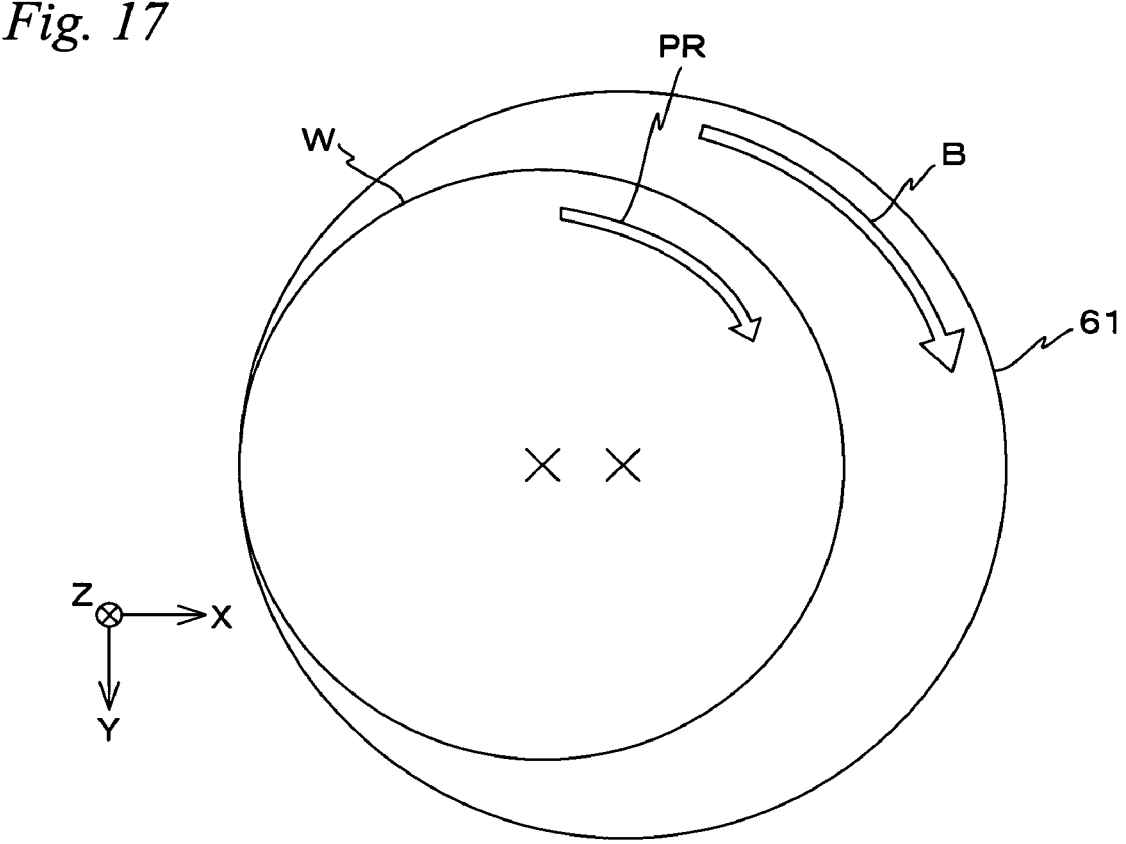
FIG. 17 is a view (No. 4) used to explain an action of the generation device in FIG. 12.

Incidentally, in the case where the liquid/foreign material adheres the vicinity of the center of wafer W, as shown in FIG. 17 as an example, the rotation center of wafer W and the center of elastic stator 61 can be displaced.

Further, the rotation of wafer W and the tilt of wafer W may be used in combination. By using both, the liquid/foreign material adhering on wafer W can be favorably removed.

Then, the liquid removed from wafer W is drained to the outside of chamber 35 by liquid suction device 39. Accordingly, the humidity within chamber 35 does not vary much. Further, when shutters 36A and 37A are opened, the humid gas is not discharged to the outside of chamber 35.

Figure 18A:
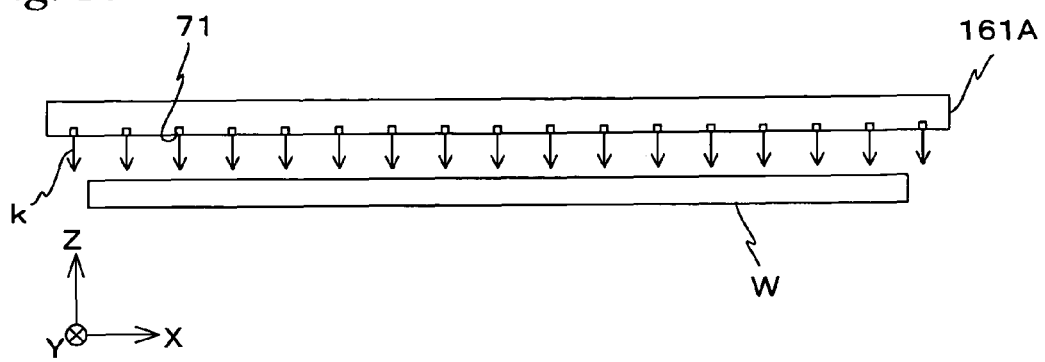
FIG. 18A and FIG. 18B are views each used to explain an elastic stator having gas supply openings.
Figure 18B:
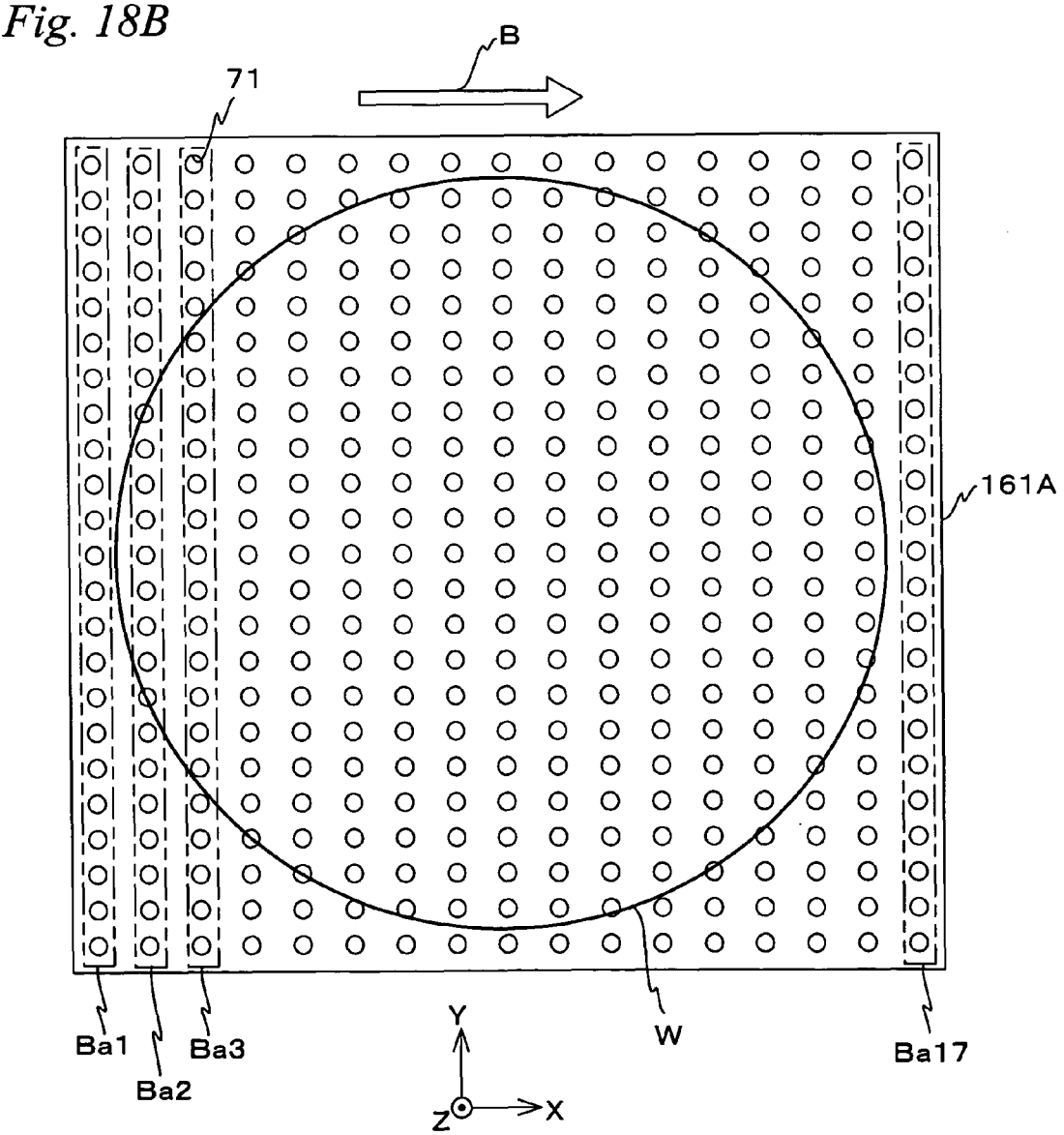

Incidentally, instead of elastic stator 61, as shown in FIGS. 18A and 18B as an example, an elastic stator 161A of a rectangular shape having a surface on the −Z side on which a plurality of gas supply openings 71 are formed may be used. In this case, a gas supply device (not shown) that blows off gas K toward the surface of wafer W from a plurality of gas supply openings 71 is further arranged. Here, a group of gas supply openings in a line in the Y-axis direction is to be one block, and the blocks sequentially arranged to the +X direction are a first block Ba1, a second block Ba2, a third block Ba3, . . . , a seventeenth block Ba17. Then, according to the travelling of flexure travelling wave B, gas blowing from the first block Ba1 is started, and then gas blowing from the second block Ba2 is started, and subsequently, gas blowing from the third block Ba3 to the seventeenth block Ba17 is sequentially started. Further, the gas blowing from the first block Ba1 is stopped after a predetermined time has elapsed from the start of gas blowing from the first block Ba1. Similarly, the gas blowing from the second block Ba2 is stopped after a predetermined time has elapsed from the start of gas blowing from the second block Ba2. Similarly, regarding the remaining blocks as well, the gas blowing from the block is stopped after a predetermined period of time has elapsed from the start of its gas blowing. With this operation, the liquid/foreign material adhering on wafer W can be removed in a short period of time. Incidentally, the number of blocks is not limited to 17. In this case, wafer W and elastic stator 161A may be tilted in the travelling direction of flexure travelling wave B.

Figure 19A:
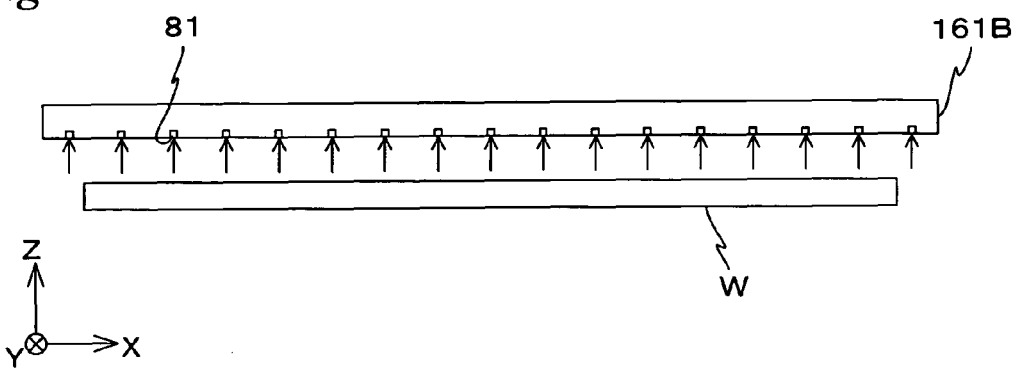
FIG. 19A and FIG. 19B are views each used to explain an elastic stator having suction openings.
Figure 19B:
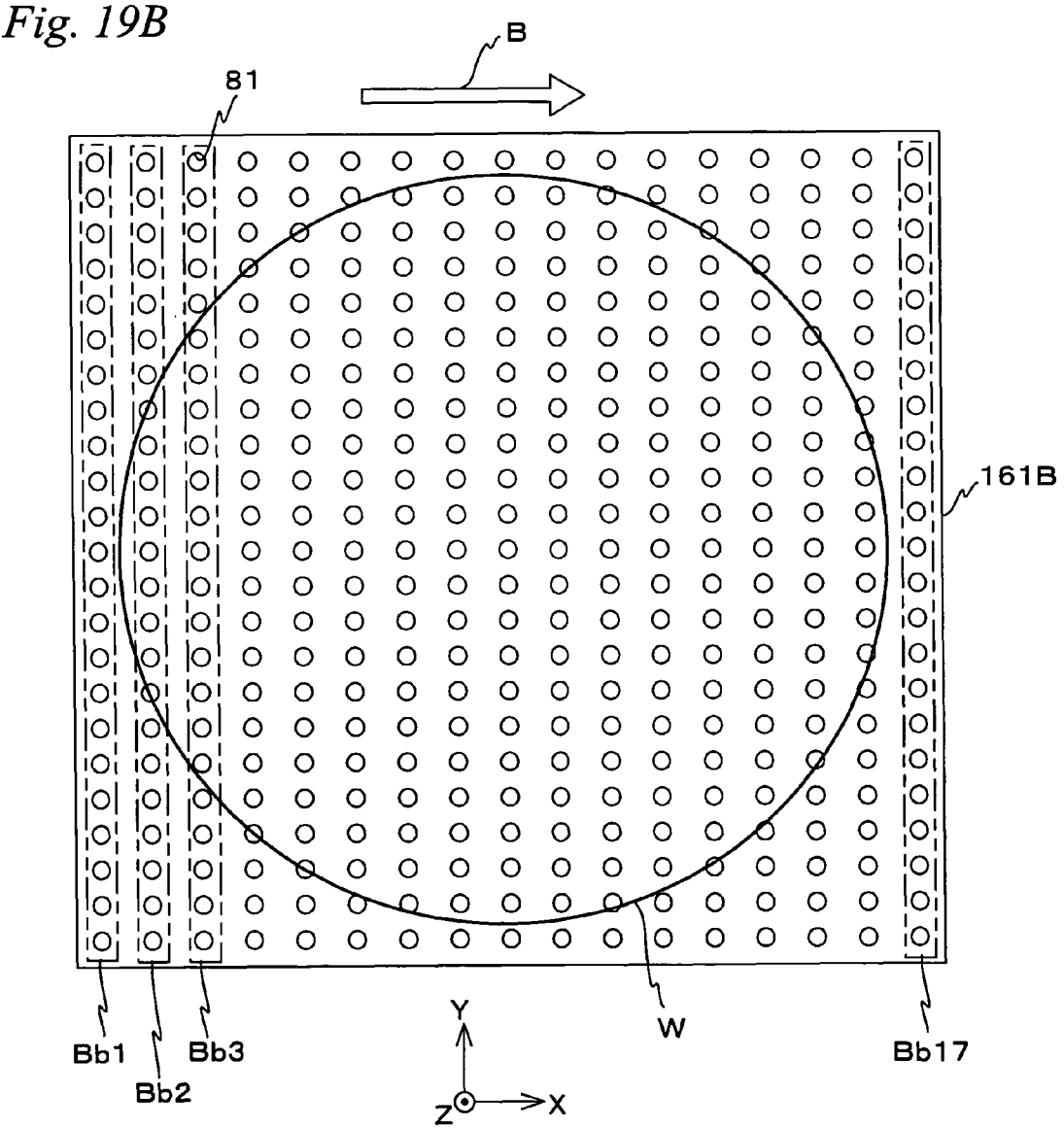

Further, instead of elastic stator 61, as shown in FIGS. 19A and 19B, an elastic stator 161B of a rectangular shape having a surface on the −Z side on which a plurality of suction openings 81 are formed may also be used. In this case, a suction device (not shown) that sucks the liquid or the like adhering on the surface of wafer W through a plurality of suction openings 81 is further arranged. Here, a group of suction openings in a line in the Y-axis direction is to be one block, and the blocks sequentially arranged to the +X direction are to be a first block Bb1, a second block Bb2, a third block Bb3, . . . , a seventeenth block Bb17. Then, according to the travelling of flexure travelling wave B, suction of the first block Bb1 is stared, and then suction of the second block Bb2 is started, and subsequently, suction of the third block Bb3 to the seventeenth block Bb17 is sequentially started. Further, the suction of the first block Bb1 is stopped after a predetermined time has elapsed from the start of suction of the first block Bb1. Similarly, the suction of the second block Ba2 is stopped after a predetermined time has elapsed from the start of suction of the second block Bb2. Similarly, regarding the remaining blocks as well, the suction of the block is stopped after a predetermined period of time has elapsed from the start of its suction. With this operation, the liquid/foreign material adhering on wafer W can be removed in a short period of time. Incidentally, the number of blocks is not limited to 17. In this case, wafer W and elastic stator 161B may be tilted in the travelling direction of flexure travelling wave B.

Further, instead of liquid suction device 39, or together with liquid suction device 39, a drying device that supplies dry gas into chamber 35 can also be arranged. With the drying device, removal of liquid LQ adhering on wafer W can be enhanced.

<<Operation of Semiconductor Manufacturing System>>

Next, an operation of semiconductor manufacturing system 100 having the configuration described above will be explained using flowcharts in FIGS. 20 to 24. Incidentally, a wafer processing process and an assembly process will be explained here.

Figure 23:
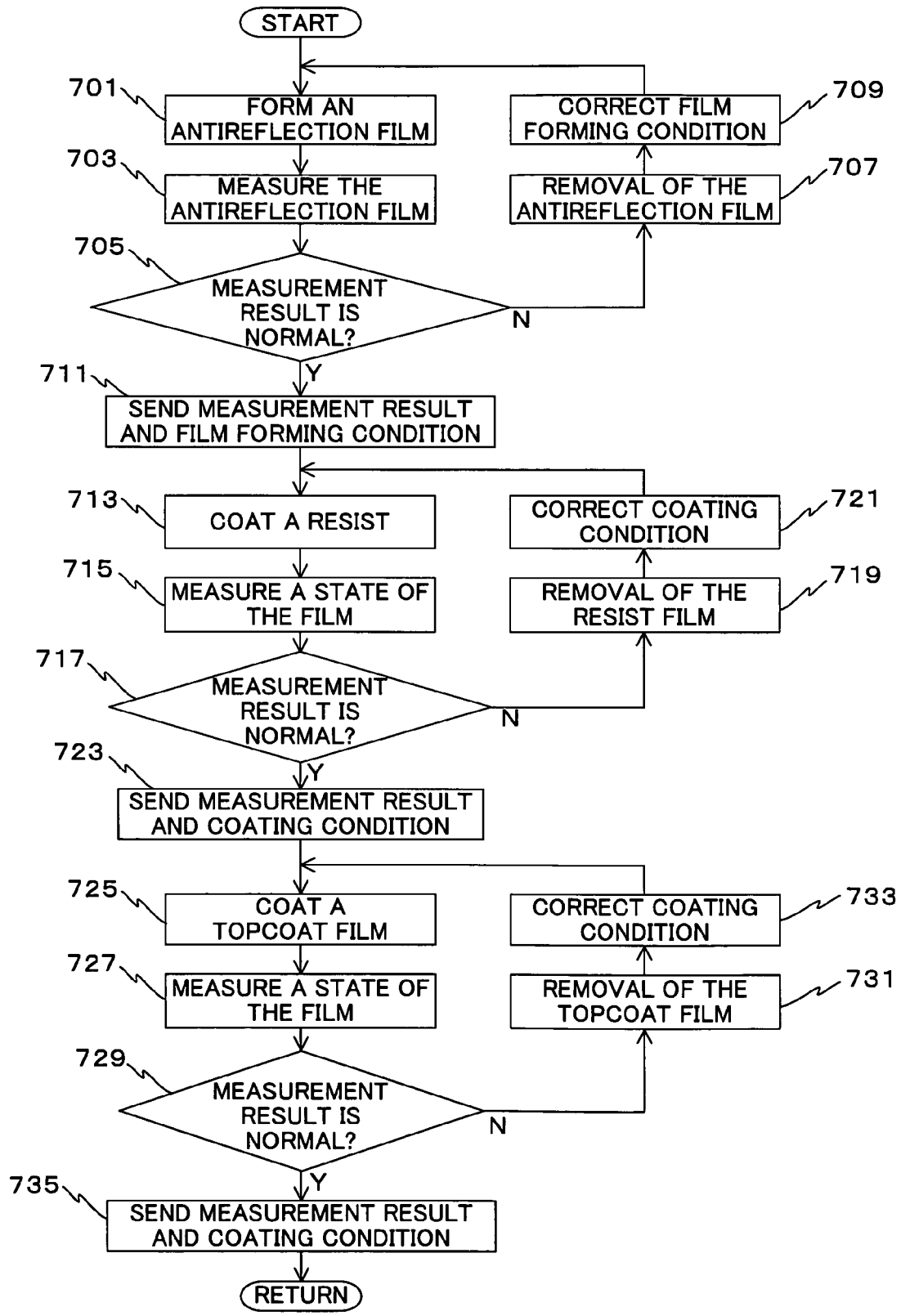
FIG. 23 is a flowchart (No. 4) used to explain an operation of the semiconductor manufacturing system in FIG. 1.
Figure 24:
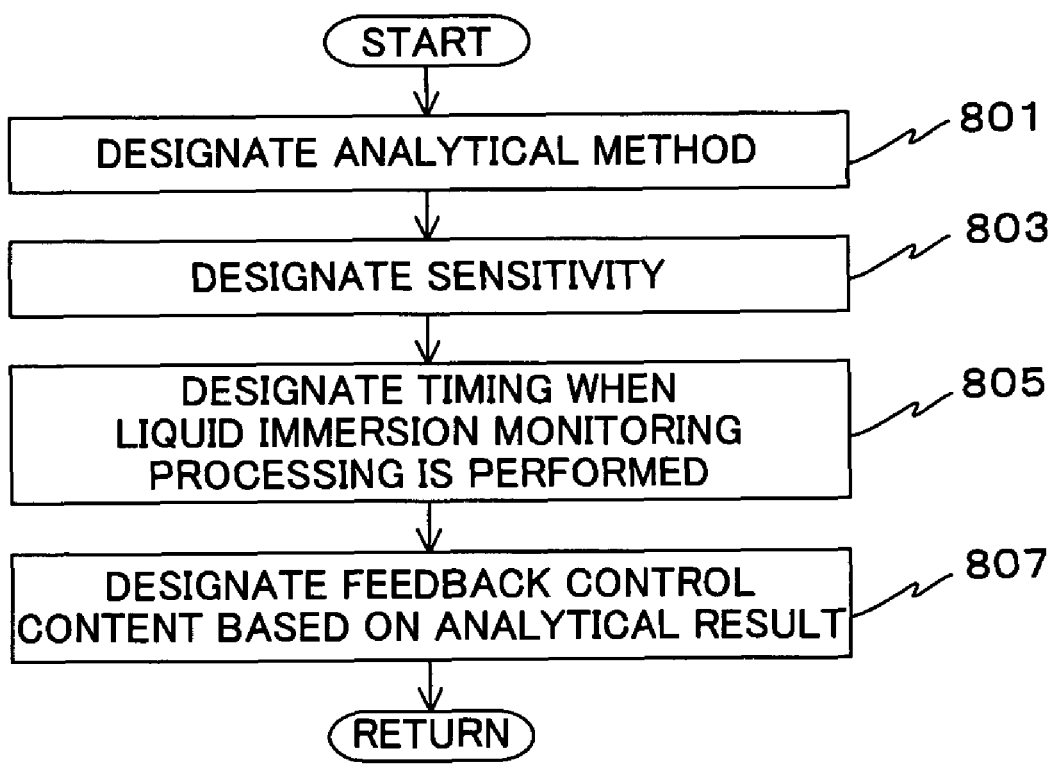
FIG. 24 is a flowchart (No. 5) used to explain an operation of the semiconductor manufacturing system in FIG. 1.
Figure 25:
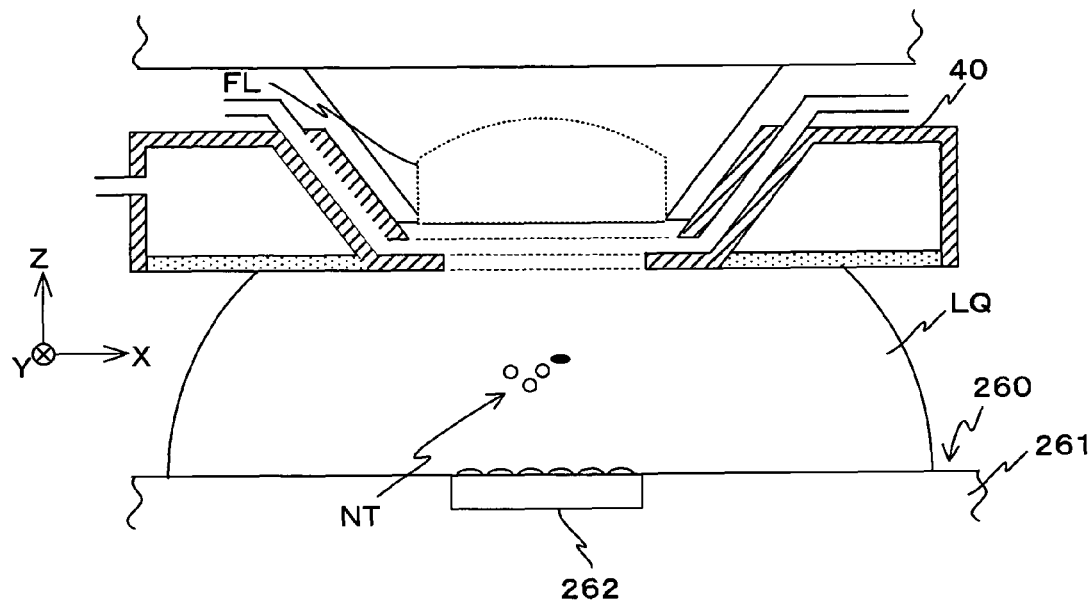
FIG. 25 is a view used to explain an operation of the semiconductor manufacturing system in FIG. 1.

In the first step, step 401, film forming/resist processing to wafer W is performed in coater/developer 111. In this film forming/resist processing, the processing (steps 701 to 735) shown in a flowchart of FIG. 23 is performed.

In step 701, wafer W is carried to coater/developer 111 and an antireflection film is formed on wafer W.

In the next step, step 703, the measurement device of coater/developer 111 measures the antireflection film on wafer W. Here, as an example, a film forming state including at least one of a film thickness of the antireflection film, a variation state of the film thickness, and flatness of the film is measured.

In the next step, step 705, based on the measurement result of the film forming state, whether or not the antireflection film is normal is judged. Then, in the case where the antireflection film is normal, the judgment in step 705 is affirmative, and the procedure proceeds to step 711. On the other hand, in the case where the antireflection film is not normal, the judgment in step 705 is negative, and the procedure proceeds to step 707.

In step 707, the antireflection film is removed.

In the next step, step 709, based on the measurement result of the antireflection film, the film forming conditions of the antireflection film are corrected. Then, the procedure returns to step 701 described above. The film forming conditions of the antireflection film include at least one of a film material, a film forming method, a targeted film thickness, film thickness uniformity, film forming environment, and a coating condition of the film material.

Hereinafter, the processing in steps 701 to 709 is repeated until the judgment in step 705 is affirmative. Then, if the antireflection film is normal, the judgment in step 705 is affirmative, and the procedure proceeds to step 711.

In step 711, the measurement result and the film forming conditions of the antireflection film are sent to analytical system 107, wafer measurement/inspection instrument 109, and the like. In this case, information on an operating state including environmental information such as the temperature, the humidity, the pressure or the like on the film forming processing may also be sent.

In the next step, step 713, a resist is coated on the antireflection film.

In the next step, step 715, the measurement device of coater/developer 111 measures a state of the films (the antireflection film+the resist film) on wafer W. In this case, as an example, a state of the films including at least one of a film thickness of the films, a variation state of the film thickness, and flatness of the films is measured.

In the next step, step 717, based on the measurement result of the state of the films, whether or not the state of the films on wafer W is normal is judged. Then, in the case where the state of the films is normal, the judgment in step 717 is affirmative and the procedure proceeds to step 723. On the other hand, in the case where the state of the films is not normal, the judgment herein is negative and the procedure proceeds to step 719.

In step 719, the resist film is removed.

In the next step, step 721, based on the measurement result of the state of the films, the coating conditions of the resist are corrected.

Then, the procedure returns to step 713 described above.

Hereinafter, the processing in steps 713 to 721 is repeated until the judgment in step 717 is affirmative. Then, if the state of the films is normal, the judgment in step 717 is affirmative, and the procedure proceeds to step 723.

In step 723, the measurement result of the state of the films and the coating conditions of the resist are sent to analytical system 107, wafer measurement/inspection instrument 109, and the like. In this case, information on an operating state including environmental information such as the temperature, the humidity, the pressure or the like on the resist coating processing may also be sent.

In the next step, step 725, a topcoat film is coated on wafer W on which the resist film has been coated.

In the next step, step 727, the measurement device of coater/developer 111 measures a state of the films (the antireflection film+the resist film+the topcoat film) on wafer W. In this case, as an example, a state of the films including at least one of a film thickness of the films, a variation state of the film thickness, and flatness of the films is measured.

In the next step, step 729, based on the measurement result of the state of the films, whether or not the state of the films on wafer W is normal is judged. In the case where the state of the films is normal, the judgment in step 729 is affirmative and the procedure proceeds to step 735. On the other hand, in the case where the state of the films is not normal, the judgment in step 729 is negative and the procedure proceeds to step 731.

In step 731, the topcoat film is removed.

In the next step, step 733, based on the measurement result of the state of the films, the coating conditions of the topcoat are corrected. Then, the procedure returns to step 725 described above.

Hereinafter, the processing in steps 725 to 733 is repeated until the judgment in step 729 is affirmative. Then, if the state of the films is normal, the judgment in step 729 is affirmative, and the procedure proceeds to step 735.

Figure 20:
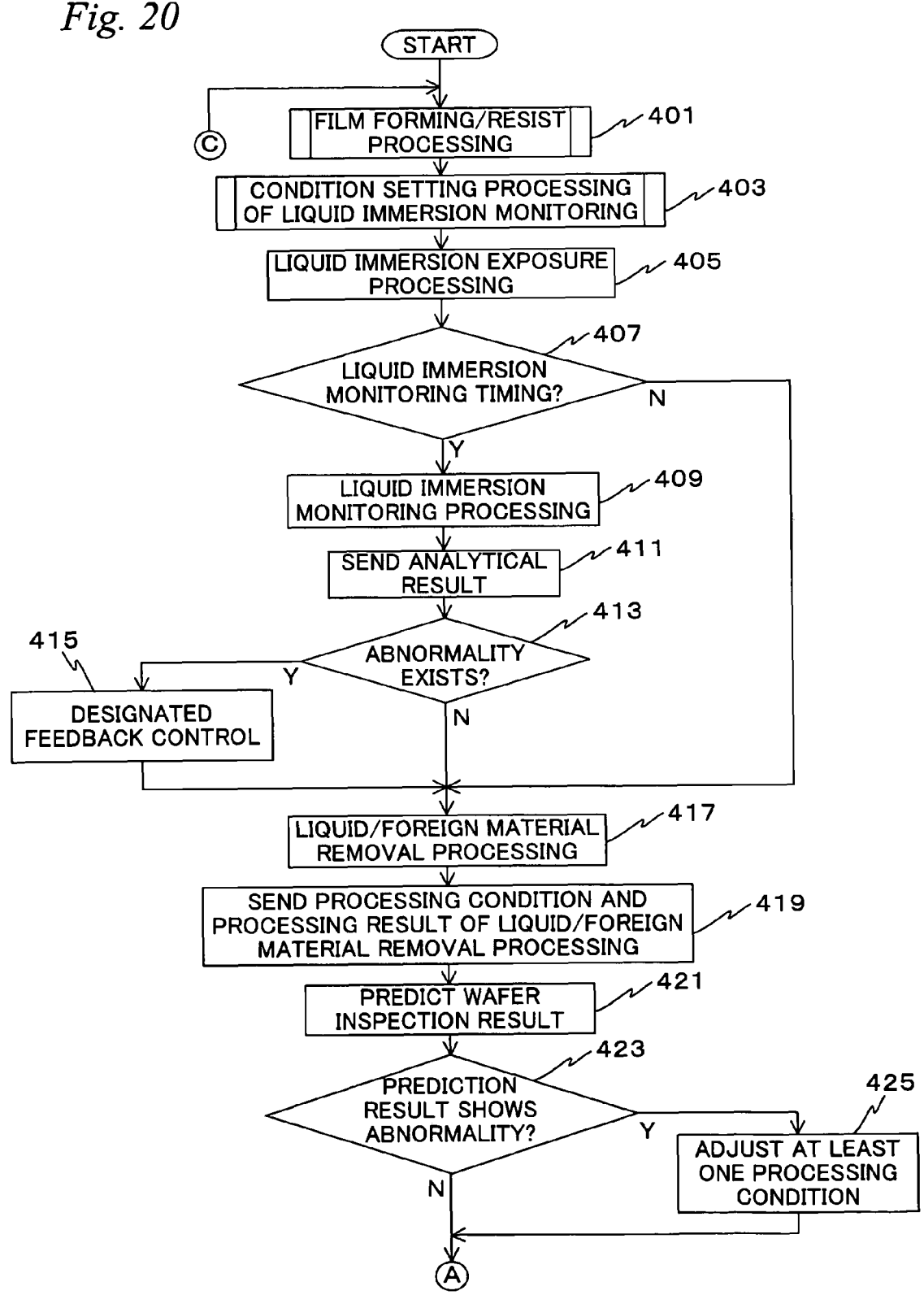
FIG. 20 is a flowchart (No. 1) used to explain an operation of the semiconductor manufacturing system in FIG. 1.
Figure 21:
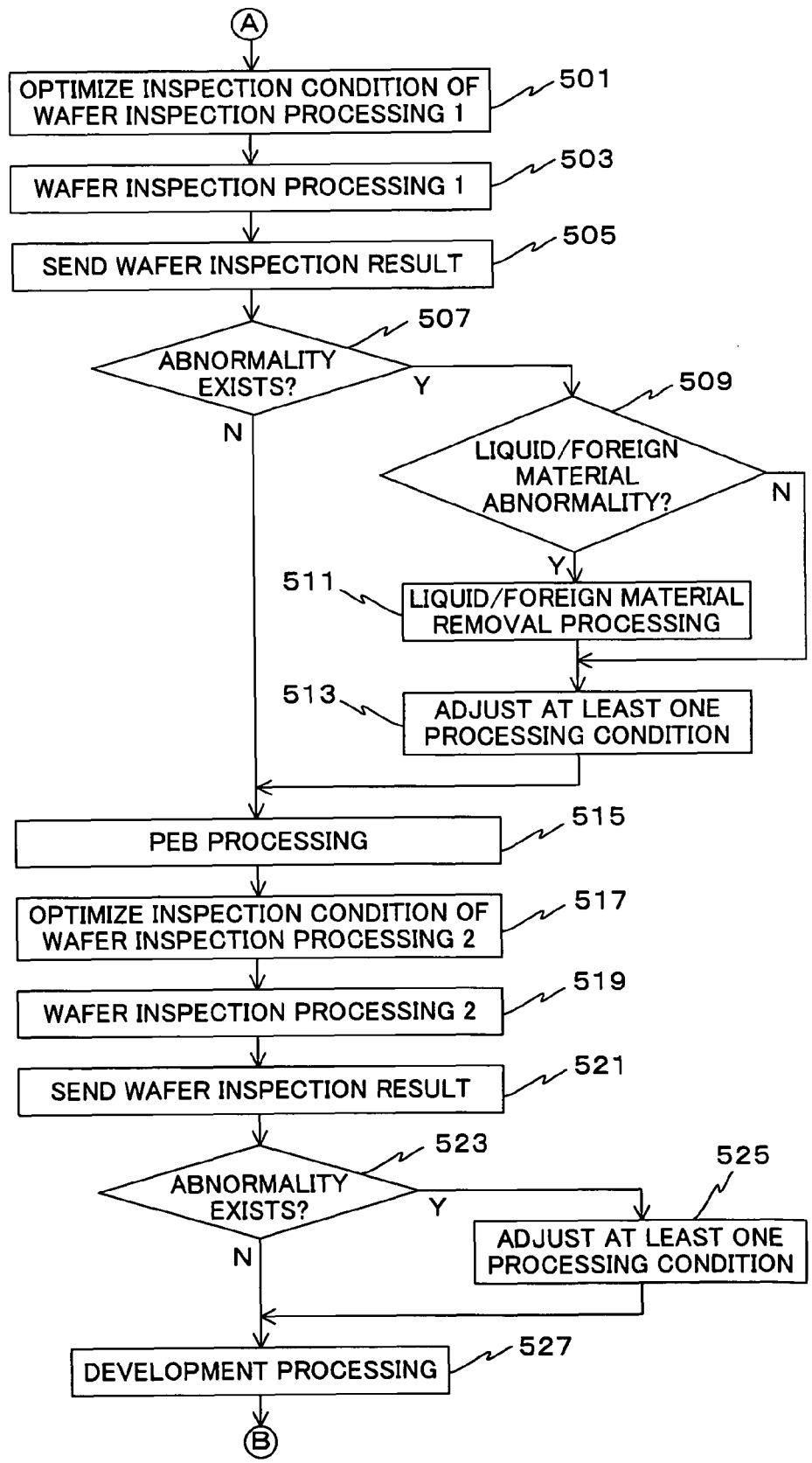
FIG. 21 is a flowchart (No. 2) used to explain an operation of the semiconductor manufacturing system in FIG. 1.
Figure 22:
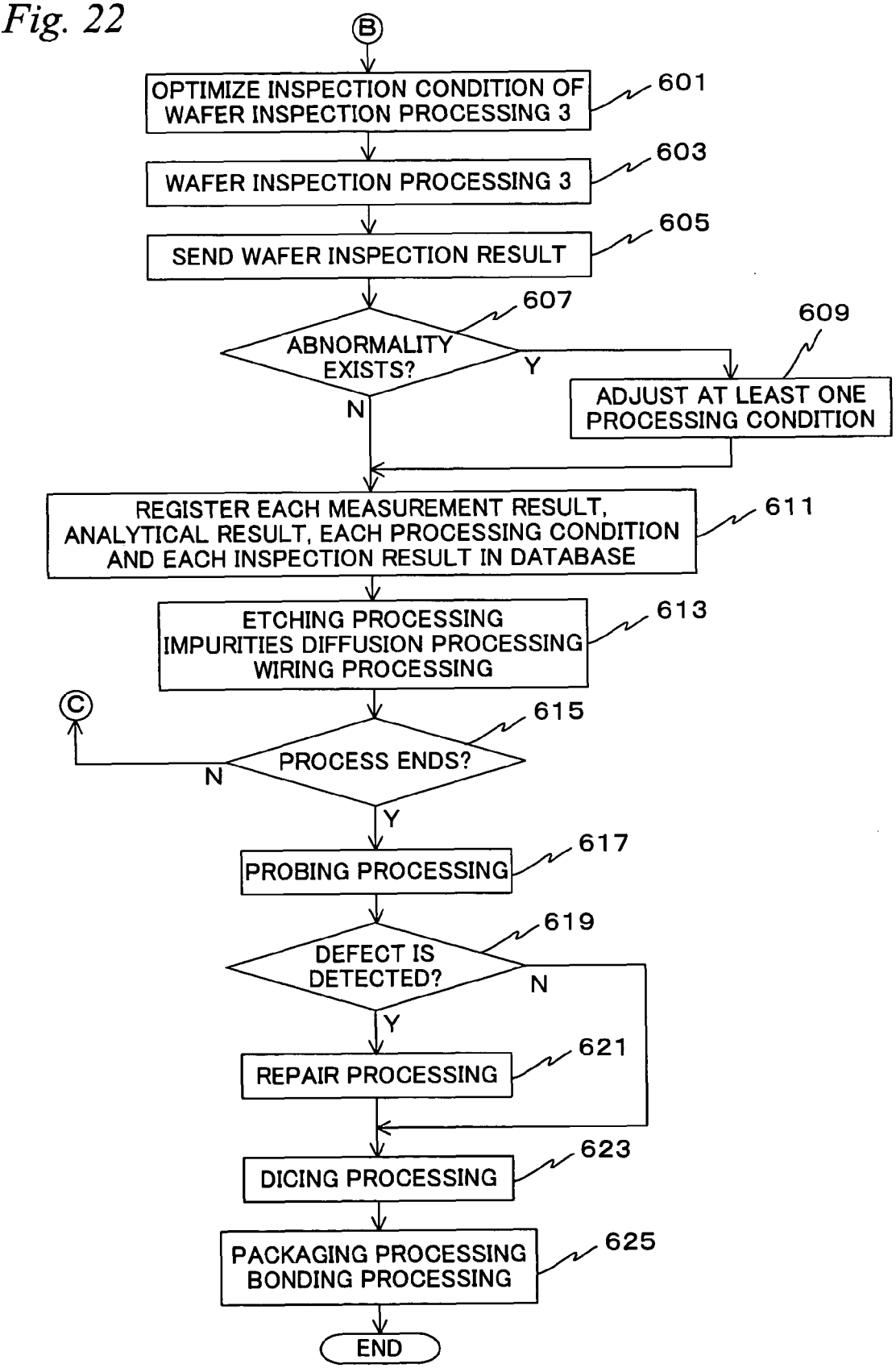
FIG. 22 is a flowchart (No. 3) used to explain an operation of the semiconductor manufacturing system in FIG. 1.

In step 735, the measurement result of the state of the films and the coating conditions of the topcoat are sent to analytical system 107, wafer measurement/inspection instrument 109, and the like. In this case, information on an operating state including environmental information such as the temperature, the humidity, the pressure or the like on the topcoat coating processing may also be sent. With this operation, the film forming/resist processing is finished, and the procedure returns to step 403 in the main routine (FIG. 20).

In step 403, condition setting processing of the liquid immersion monitoring is performed in exposure apparatus main section S. In the condition setting processing of the liquid immersion monitoring, the processing shown in a flowchart of FIG. 24 (steps 801 to 807) is performed. Incidentally, the condition setting processing of the liquid immersion monitoring may be performed by a worker replying to the content displayed on a display device (not shown), that is, may be performed interactively via an input device (not shown), or main controller 42 may perform the condition setting processing in accordance with the exposure conditions from exposure process management controller 103.

In step 801, the analytical method in analytical device 263 of liquid immersion monitor device 260 is designated. In this case, at least one of the following methods (1) to (3) is designated and notified to analytical device 263 and the like.

(1) Z-Axis Direction Image Comparison Method

The Z-axis direction image comparison method is a method of comparing observation results at a plurality of positions that are different from one another in the Z-axis direction. Specifically, six pieces of image information, which are obtained from the output signals from the six line sensors (267A to 267F) respectively, are compared to one another, and for example, in the case where the image information obtained from the output signal of line sensor 267C is different at a permissible level or more from the other five pieces of image information, the judgment is made that a foreign material exists in the vicinity of a position which is distance d3 away from the surface of wafer W. This judgment is possible because there is extremely low probability that foreign materials exist at positions subject to observation of all the line sensors at the same time. Incidentally, it is preferable that the six pieces of image information described above are each the image information at the same position within the XY plane.

(2) Reference Image Comparison Method

The reference image comparison method is a method of comparing image information (hereinafter, referred to as "reference image information A") at the time when a foreign material does not exists, which has been acquired in advance by experiment or simulation, and an observation result. Specifically, each of the six pieces of image information descried above and reference image information A are compared, and for example, the difference between the image information obtained from the output signal of line sensor 267C and reference image information A is at a permissible level or more, the judgment is made that a foreign material exists in the vicinity of the position which is distance d3 away from the surface of wafer W.

(3) Feature Extraction Method

The feature extraction method is a method of comparing image information at the time of a foreign material exists which has been acquired in advance by experiment or simulation, such as image information (hereinafter, referred to as "reference image information B") at the time when bubbles exits and image information (hereinafter, referred to as "reference image information C") at the time when a particle exits, and an observation result. Specifically, each of the six pieces of image information and the reference image information such as reference image information B and reference image information C are compared. Then, for example, in the case where the image information obtained from the output signal of line sensor 267C and reference image information B are similar within a range set in advance, the judgment is made that bubbles exist in the vicinity of the position which is distance d3 away from the surface of wafer W. Incidentally, the image information (reference image information B) at the time when bubbles exist has a feature that a circular bright section exists outside the periphery of the bubbles, whereas inside the bubbles a pattern different from that of the periphery exists with the dark section as a base.

Incidentally, the methods of the above (1) to (3) may also be employed in combination as needed.

In the next step, step 803, the analytical sensitivity of liquid immersion monitor device 260 is designated in accordance with the targeted shape accuracy (targeted linewidth accuracy) of a pattern to be formed on wafer W. For example, in the case where high linewidth accuracy is required, the analytical sensitivity of liquid immersion monitor device 260 is set high so that even a fine or a little amount of foreign material can be judged as abnormal. On the contrary, in the case where the relatively low linewidth accuracy is permissible, the analytical sensitivity of liquid immersion monitor device 260 is set so that a foreign material that is less than or equal to a level set in advance is not recognized as a foreign material. The content designated here are notified to analytical device 263 and the like. Further, closer from the surface of the wafer a foreign material exists, more easily the foreign material is transferred to the resist, and therefore, the setting of the analytical sensitivity for judging a foreign material as abnormal can be changed with respect to each position subject to observation in the liquid immersion, that is, with respect to each line sensor.

In the next step, step 805, timing at which liquid immersion monitoring processing is performed is designated. In this case, as the timing at which the liquid immersion monitoring processing is performed, (1) per a predetermined number of substrate processing, (2) per a predetermined number of lot processing, (3) at a predetermined time interval, (4) every time when a liquid immersion area is newly formed, and the like can be given. Incidentally, each of the timing of the above (1) to (4) may also be employed in combination as needed. The content designated here are stored in the working memory of main controller 42.

In the next step, step 807, the content of feedback control based on the analytical result at liquid immersion monitor device 260 is designated. In this case, as the content of the feedback control, (1) entire or partial replacement of liquid LQ in the liquid immersion area, (2) change of waiting time for supplying liquid LQ to the liquid immersion area, (3) change of stabilization time of liquid LQ in the liquid immersion area, (4) change of a supply quantity of liquid LQ to the liquid immersion area, (5) change of supply speed of liquid LQ to the liquid immersion area, (6) change of exposure conditions such as exposure dose, exposure scan speed and an focus offset, (7) wafer skip, (8) suspension of lot processing, (9) change of processing conditions at coater/developer 111, (10) change of measurement conditions and inspection conditions at wafer measurement/inspection instrument 109, and the like can be given. Incidentally, each of the feedback control of the above (1) to (10) may also be employed in combination as needed. The content designated here is notified to analytical system 107 and the like. With this operation, the condition setting processing of the liquid immersion monitoring is finished, and the procedure returns to step 405 of the main routine (FIG. 20).

In step 405, wafer W is carried to exposure apparatus main section S, and liquid immersion exposure processing is performed in exposure apparatus main section S. In this case, exposure apparatus main section S irradiates exposure light EL having passed through reticle R on wafer W via projection optical system PL and liquid LQ in the liquid immersion area, and projects a pattern image of reticle R to wafer W.

In the next step, step 407, whether or not this is the timing designated in the condition setting processing of the liquid immersion monitoring described above is judged by main controller 42. Then, if this is not the designated timing, the judgment in step 407 is negative, and the procedure proceeds to step 417. On the contrary, if this is the designated timing, the judgment in step 407 is affirmative, and the procedure proceeds to step 409.

In step 409, the liquid immersion monitoring processing is performed in liquid immersion monitor device 260. Main controller 42 moves wafer stage WST so that base material 261 moves in the X-axis direction shown in FIG. 6, while measuring positional information of wafer stage WST on which liquid immersion monitor device 260 is held, using laser interferometer 17, so as to make image information obtained from the output signals from the respective line sensors be of the same position within the XY plane.

In the next step, step 411, the analytical result at analytical device 263 is sent to main controller 42, analytical system 107, wafer measurement/inspection instrument 109 and the like.

In the next step, step 413, in analytical system 107, whether abnormality exists or not is judged based on the analytical result received from analytical device 263. Then, if the abnormality does not exist, the judgment in step 413 is negative, and the procedure proceeds to step 417. On the other hand, if a foreign material NT such as bubbles or a particle exists in the liquid immersion area and the analytical result is abnormal, the judgment in step 413 is affirmative, and the procedure proceeds to step 415.

In step 415, the content of the feedback control set in step 807 described above is sent from analytical system 107 to main controller 42. Then, in exposure apparatus main section S, the content of the feedback control received from analytical system 107 is executed.

In the next step, step 417, wafer W is carried to removal device T, and the removal processing of liquid/foreign material described earlier is performed.

In the next step, step 419, the processing conditions and the processing results (the observation results of the observation device) of the liquid/foreign material removal are sent from removal device T to analytical system 107, wafer measurement/inspection instrument 109, and the like.

In the next step, step 421, analytical system 107 predicts the inspection result of wafer W by wafer measurement/inspection instrument 109, based on at least one of each measurement result, the film forming conditions and the respective coating conditions in the film forming/resist processing; the liquid immersion exposure conditions in exposure apparatus 105; the monitoring results in the liquid immersion monitoring processing; and the processing conditions and the processing results of liquid/foreign material removal in removal device T.

Incidentally, hereinafter, "at least one of: each measurement result, the film forming conditions, and the respective coating conditions in the film forming/resist processing described previously; the liquid immersion exposure conditions in exposure apparatus 105; the monitoring results in the liquid immersion monitoring processing; and the processing conditions and the processing results of liquid/foreign material removal in removal device T" is also referred to as "at least one of wafer processing conditions/processing results" for the sake of convenience.

For example, the inspection result of wafer W by wafer measurement/inspection instrument 109 may be predicted, based on at least one of each measurement result, the film forming conditions, and the respective coating conditions of the film forming/resist processing described previously, by referring to a correlation between at least one of each measurement result, the film forming conditions, and the respective coating conditions of the film forming/resist processing described previously, and abnormality detection in wafer inspection by wafer measurement/inspection instrument 109, which has been acquired in advance.

Further, the inspection result of wafer W by wafer measurement/inspection instrument 109 may be predicted based on the monitoring result of the liquid immersion monitoring processing described previously, by referring to a correlation between the monitoring result of the liquid immersion monitoring processing described previously and abnormality detection in wafer inspection by wafer measurement/inspection instrument 109, which has been acquired in advance. Specifically, the influence that an exposure pattern is received can be derived from information on a type, a position, a size, a shape, the number and the like of a foreign material in the liquid immersion area, and information on a position of contamination, the degree of contamination of the like of optical element FL. Then, defect of the exposure pattern can be predicted from foreign material information and contamination information of optical element FL obtained by liquid immersion monitor device 260. Further, for example, defect of the exposure pattern can also be predicted from information on foreign material on the topcoat film and information on liquid LQ infiltrating the film(s).

Further, the inspection result of wafer W by wafer measurement/inspection instrument 109 may be predicted based on the processing result of the liquid/foreign material removal described previously, by referring to a correlation between the processing result of the liquid/foreign material removal described previously and abnormality detection in wafer inspection by wafer measurement/inspection instrument 109, which has been acquired in advance.

In the next step, step 423, analytical system 107 judges whether or not the prediction result shows "abnormality of wafer W will be detected in wafer inspection by wafer measurement/inspection instrument 109". Then, if the prediction result shows "abnormality of wafer W will not be detected in wafer inspection by wafer measurement/inspection instrument 109", the judgment in step 423 is negative, and the procedure proceeds to step 501. On the other hand, if the prediction result shows "abnormality of wafer W will be detected in wafer inspection by wafer measurement/inspection instrument 109", the judgment in step 423 is affirmative, and the procedure proceeds to step 425.

In step 425, analytical system 107 instructs adjustment of at least one of the film forming conditions and coating conditions in coater/developer 111, the liquid immersion exposure conditions in exposure apparatus 105, and the liquid/foreign material removal processing conditions in removal device T.

Incidentally, hereinafter, "at least one of the film forming conditions and coating conditions in coater/developer 111, the liquid immersion exposure conditions in exposure apparatus 105, and the liquid/foreign material removal processing conditions in removal device T" is also referred to as "at least one of the wafer processing conditions" for the sake of convenience.

Incidentally, the liquid immersion exposure conditions include at least one of a supply condition at the time of supplying liquid LQ to the liquid immersion area, a recovery condition at the time of recovering liquid LQ from the liquid immersion area, a movement condition of wafer W, a size of the liquid immersion area and a shape of the liquid immersion area. As a specific example, main controller 42 (1) increase the degassing capability of the degassing device of liquid supply device 11, (2) adjusts a supply quantity per unit time of liquid LQ supplied from supply opening 12, or (3) adjusts a recovery quantity per unit time via recovery opening 22, in order to suppress generation of bubbles in liquid LQ that forms the liquid immersion area. Also by adjustment of the size and the shape of the liquid immersion area, generation of bubbles in the liquid immersion area, and infiltrating of liquid LQ into the films formed on wafer W (which depends on the contact time of the films and liquid LQ) can be suppressed.

The foregoing movement conditions of wafer W include at least one of a movement speed, an acceleration, a deceleration, a movement direction, a movement trajectory and a movement distance of wafer W with respect to liquid LQ in the liquid immersion area, and a time when each position of wafer W is immersed in liquid LQ, and focus/leveling conditions.

Further, the processing conditions of the liquid/foreign material removal include at least one of an on/off condition of the flexure travelling wave, a rotational speed of wafer W, a tilt angle of wafer W, a blowing condition of gas in the case of using elastic stator 161A, a suction condition in the case of using elastic stator 161B, and a drying condition in the case of using the drying device.

In the next step, step 501, wafer measurement/inspection instrument 109 optimizes inspection conditions of wafer inspection processing No. 1 in which wafer W to which the liquid immersion exposure has been performed is inspected, based on information on "at least one of the wafer processing conditions/processing results". The inspection conditions in this case include at least one of an inspection position and inspection sensitivity of wafer W.

In the next step, step 503, wafer W is carried to wafer measurement/inspection instrument 109, in which the wafer inspection processing No. 1 is performed. In this case, based on the optimal inspection conditions, appearance inspection of wafer W is performed.

In the next step, step 505, the inspection result of the wafer inspection processing No. 1 is sent to analytical system 107 and the like.

In the next step, step 507, analytical system 107 judges whether or not wafer W has abnormality, based on the inspection result of the wafer inspection processing No. 1. Then, if there is no abnormality, the judgment in step 507 is negative and the procedure proceeds to step 515. On the other hand, if wafer W has abnormality, the judgment in step 507 is affirmative and the procedure proceeds to step 509.

In step 509, analytical system 107 judges whether or not there is a possibility that the liquid/foreign material on wafer W adversely affects wafer W, based on the inspection result of the wafer inspection processing No. 1. The judgment result in this step is sent to removal device T. Then, if there is no possibility that the liquid/foreign material on wafer W adversely affects wafer W, the judgment in step 509 is negative, the procedure proceeds to step 513. On the contrary, if there is a possibility that the liquid/foreign material on wafer W adversely affects wafer W, the judgment in step 509 is affirmative, the procedure proceeds to step 511.

In step 511, wafer W is carried to removal device T, and the liquid/foreign material removal processing is performed again.

In the next step, step 513, analytical system 107 instructs adjustment of "at least one of the wafer processing conditions" so as to avoid the abnormality.

In the next step, step 515, wafer W is carried to coater/developer 111, in which the PEB processing is performed.

In the next step, step 517, wafer measurement/inspection instrument 109 optimizes the inspection conditions of wafer inspection processing No. 2 in which wafer W to which the PEB processing has been performed is inspected, based on information on "at least one of the wafer processing conditions/processing results". The inspection conditions in this case include at least one of the inspection position and the inspection sensitivity of wafer W.

In the next step 519, wafer W is carried to wafer measurement/inspection instrument 109, in which the wafer inspection processing No. 2 is performed. In this case, the appearance inspection of wafer W is performed based on the optimal inspection conditions.

In the next step, step 521, the inspection result of the wafer inspection processing No. 2 is sent to analytical system 107 and the like.

In the next step, step 523, analytical system 107 judges whether or not wafer W has abnormality, based on the inspection result of the wafer inspection processing No. 2. Then, if there is no abnormality, the judgment in step 523 is negative and the procedure proceeds to step 527. On the other hand, if wafer W has abnormality, the judgment in step 523 is affirmative and the procedure proceeds to step 525.

In step 525, analytical system 107 instructs adjustment of "at least one of the wafer processing conditions" so as to avoid the abnormality.

In the next step, step 527, wafer W is carried to coater/developer 111, in which the development processing is performed.

In the next step, step 601, wafer measurement/inspection instrument 109 optimizes the inspection conditions of wafer inspection processing No. 3 in which wafer W to which the development processing has been performed is inspected, based on information on "at least one of the wafer processing conditions/processing results". The inspection conditions in this case include at least one of an inspection position and inspection sensitivity of wafer W.

In the next step, step 603, wafer W is carried to wafer measurement/inspection instrument 109, in which the wafer inspection processing No. 3 is performed. In this case, based on the optimal inspection conditions, inspection of an exposure pattern (resist pattern) on wafer W is performed.

In the next step, step 605, the inspection result of the wafer inspection processing No. 3 is sent to analytical system 107.

In the next step, step 607, analytical system 107 judges whether or not wafer W has abnormality, based on the inspection result of the wafer inspection processing No. 3. Then, if there is no abnormality, the judgment in step 607 is negative and the procedure proceeds to step 611. On the other hand, if wafer W has abnormality, the judgment in step 607 is affirmative and the procedure proceeds to step 609.

In step 609, analytical system 107 instructs adjustment of "at least one of the wafer processing conditions" so as to avoid the abnormality.

In the next step, step 611, analytical system 107 registers each of the measurement results, the analytical results, each of the processing conditions, each of the inspection results and the like in the correlation database. The correlation database is referred to when predicting the inspection result of wafer W as is described earlier. Further, in this case, based on the correlation database, a correlation between at least one of each measurement result, the film forming conditions, and the respective coating condition of the film forming/resist processing, and abnormality detection in inspection by the inspection device; a correlation between the monitoring result during the liquid immersion monitoring processing and abnormality detection in inspection by the inspection device; a correlation between the processing result of the liquid/foreign material removal and abnormality detection in inspection by the inspection device; and the like are acquired.

In the next step, step 613, the etching processing by etching apparatus 115, the impurity diffusion processing by oxidation/ion-implantation apparatus 119, the wiring processing by CVD apparatus 113, the planarization processing by CMP apparatus 117, and the like are performed, as the need arises.

In the next step, step 615, whether or not the processing process to the wafer W has been finished is judged. If the processing process has not been finished, the judgment herein is negative, and the procedure returns to step 401 described previously.

Afterward, until the judgment in step 615 is affirmative, the processing in steps 401 to 615 is repeated. When the processing process to the wafer W is finished, the judgment in step 615 is affirmative, and the procedure proceeds to step 617.

In step 617, the probing processing is performed.

In the next step, step 619, whether or not defect is detected is judged. If the defect is not detected, the judgment in step 619 is negative, and the procedure proceeds to step 623. On the contrary, if the defect is detected, the judgment in step 619 is affirmative, and the procedure proceeds to step 621.

In step 621, the repair processing is performed. Specifically, the replacement processing for replacement with a redundant circuit and the like are performed.

In the next step, step 623, the dicing processing is performed.

In the next step, step 625, the packaging processing and the bonding processing are performed. Then, the operation of semiconductor manufacturing system 100 is finished.

As is obvious from the explanation above, in the embodiment, an example of the first to third programs of the present invention are executed in the programs corresponding to the flowcharts in FIGS. 20 to 24, and an example of the recording medium of the present invention is executed by the respective flash memories in which the programs corresponding to the flowcharts in FIGS. 20 to 24 are stored.

As is explained above, according to semiconductor manufacturing system 100 related to the embodiment, wafer measurement/inspection instrument 109 optimizes the inspection conditions of the wafer inspection processing No. 1 in which wafer W to which liquid immersion exposure has been performed is inspected, the inspection conditions of the wafer inspection processing No. 2 in which wafer W to which the PEB processing has been performed is inspected, and the inspection conditions of the wafer inspection processing No. 3 in which wafer W to which the development processing has been performed is inspected, respectively, based on information on "at least one of the wafer processing conditions/ processing results". With this operation, the efficient quality inspection of wafer W can be performed. Accordingly, as a consequence, the processing to wafer W can efficiently be performed.

Further, based on "at least one of the wafer processing conditions/processing results", analytical system 107 predicts the inspection result of wafer W by wafer measurement/ inspection instrument 109. Then, when the prediction results shows "abnormality of wafer W will be detected in wafer inspection by wafer measurement/inspection instrument 109", analytical system 107 instructs adjustment of "at least one of the wafer processing conditions", so as to avoid the abnormality. Accordingly, the yield can be improved.

In this case, analytical system 108 predicts the inspection result of wafer W by wafer measurement/inspection instrument 109, by referring to the correlation acquired in advance. Accordingly, the prediction accuracy can be increased.

Further, based on the inspection result of the wafer inspection processing No. 1, analytical system 107 judges whether or not there is a possibility that the liquid/foreign material on wafer W adversely affects wafer W, and sends the judgment result to removal device T. Then, if there is a possibility that the liquid/foreign material on wafer W adversely affects wafer W, removal device T performs the liquid/foreign material removal processing again. Accordingly, the yield can be improved, and as a consequence, the processing to wafer W can be efficiently performed.

In this case, if there is a possibility that the liquid/foreign material on wafer W adversely affects wafer W, removal device T can adjust the processing conditions of the liquid/ foreign material removal. Accordingly, as a consequence, the processing to wafer W can be efficiently performed.

Incidentally, in the embodiment above, the case where reticle R is a transmissive type reticle has been explained, but the type is not limited thereto, and a reflective type reticle may also be used.

Figure 26:
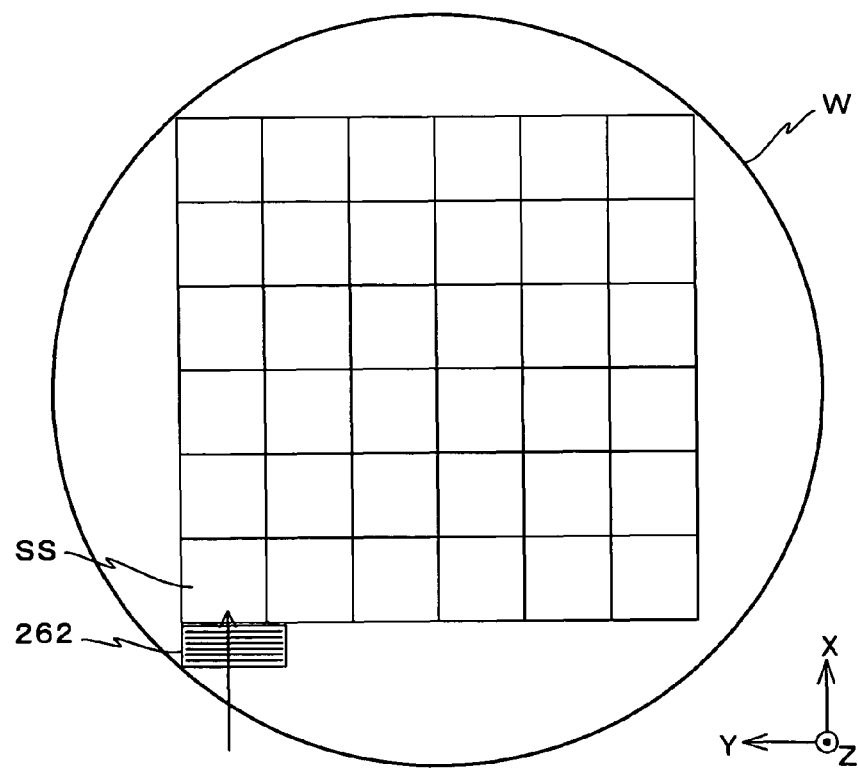
FIG. 26 is a view used to explain a wafer on which the CCD sensor module is placed.

Further, in the embodiment above, instead of using liquid immersion monitor device 260, CCD sensor module 262 may also be arranged on wafer W, as shown in FIG. 26 as an example. In this case, CCD sensor module 262 is arranged on the front side of an exposure start shot SS. With this arrangement, a liquid immersion state can be monitored during a usual exposure sequence. Further, CCD sensor module 262 may be arranged at a predetermined position on wafer stage WST. Also in this case, the liquid immersion monitoring can be performed during the exposure.

Further, in the embodiment above, the case has been explained where light source for illumination 15 is installed in the periphery portion of the liquid immersion area in order to illuminate the liquid immersion area, but the present invention is not limited thereto, and instead of light source for illumination 15, for example, a light-emitting device may be arranged on base material 261. Further, when a line sensor having the sensitivity to exposure light EL is used as the line sensor of liquid immersion monitor device 260, the liquid immersion area may be illuminated using exposure light EL.

Further, in the embodiment above, instead of wafer measurement/inspection instrument 109, an offline wafer measurement/inspection instrument may be used.

Further, in the embodiment above, an inspection device that performs appearance inspection of wafer W to which the liquid immersion exposure has been performed, an inspection device that performs appearance inspection of wafer W to which the PEB processing has been performed, and an inspection device that performs pattern inspection of wafer W to which the development processing has been performed may be difference inspection devices, respectively.

Further, in the embodiment above, at least part of the processing performed by analytical system 107 may be performed by wafer measurement/inspection instrument 109.

Further, in the embodiment above, instead of the one-dimensional line sensor of liquid immersion monitor device 260, an area sensor may also be used. In view of the area size, the processing time, the power consumption and the like of the CCD sensor, however, it is more preferable that scan imaging is performed using the one-dimensional line sensor.

Further, in the embodiment above, the case has been described where liquid immersion monitor device 260 has six one-dimensional line sensors, but the present invention is not limited thereto. Furthermore, the object plane position of each one-dimensional line sensor in the embodiment above is merely an example, and the position is not limited to the one in the embodiment above.

Further, in the embodiment above, the case has been described where liquid immersion monitor device 260 has five CCD sensor modules 262, but the present invention is not limited thereto. Further, the placement of the respective CCD sensor modules is not limited to the one in the embodiment above either.

Further, in the embodiment above, instead of each microlens of liquid immersion monitor device 260, by using a microlens with a focal distance adjustment function that can adjust a focal distance by placing a ring-shaped electrostrictive device around the microlens and adjusting the drive voltage of the electrostrictive device, the object plane position may be set for each line sensor.

Further, in the embodiment above, the case has been described where generation device 60 has the elastic stator, but generation device 60 may have a plurality of elastic stators placed on the XY plane.

Further, in the embodiment above, the case has been described where liquid LQ filled in the liquid immersion area is pure water, but the present invention is not limited thereto, and a liquid that transmits exposure light EL, has a refractive index as high as possible, has less change in the refractive index due to temperature change, has a low degree of viscosity, and is stable to optical element FL and the photoresist can be used. As the candidate for such liquid, a glycerol having a high refractive index and the like can be given, although its transmittance to the exposure light is not good.

Further, in the embodiment above, the case has been described where analytical device 263 of liquid immersion monitor device 260 performs analysis of the liquid immersion monitoring, but the present invention is not limited thereto, and for example, main controller 42 may perform analysis of the liquid immersion monitoring based on the output signal of each line sensor of liquid immersion monitor device 260.

Further, in the embodiment above, the removal subject of removal device T may be not only wafer W after the exposure processing but also wafer W before the exposure processing. That is, removal device T may be used for removing a foreign material such as a particle adhering on wafer W before the exposure processing.

Further, in the embodiment above, the case has been described where the exposure subject in exposure apparatus main body S is a semiconductor wafer for manufacturing a semiconductor, but the present invention is not limited thereto, and for example, the exposure subject may also be a glass substrate for display device, a ceramic wafer for thin film magnetic head, or an original plate (synthetic silica, silicon wafer) of a mask or a reticle that is used in an exposure apparatus. That is, exposure apparatus main section S is not limited to an exposure apparatus for manufacturing semiconductor devices, but for example, may be an exposure apparatus for manufacturing liquid crystal display devices, an exposure apparatus for manufacturing displays, an exposure apparatus for manufacturing thin film magnetic heads, an exposure apparatus for manufacturing imaging devices, an exposure apparatus for manufacturing reticles or masks, and the like.

Furthermore, a shape of the exposure subject in exposure apparatus main section S is not limited to a circular shape, but for example, may be a rectangular shape. In this case, as base material 261 of liquid immersion monitor device 260, the base material also having a rectangular shape is used.

Further, in the embodiment above, the case has been described where there is one exposure apparatus of semiconductor manufacturing system 100, but the present invention is not limited thereto, and a plurality of exposure apparatuses may be arranged.

Further, in the embodiment above, exposure apparatus main section S may be a scanning type exposure apparatus (a so-called scanning stepper) that exposes a pattern formed on reticle R to wafer W while synchronously moving reticle R and wafer W in a scanning direction. Further, exposure apparatus main section S may also be a projection exposure apparatus by a step-and-repeat method that exposes a pattern formed on reticle R in one time in a state of making reticle R and wafer W static and sequentially performs step movement of wafer W. Moreover, exposure apparatus main section S may also be an exposure apparatus by a step-and-stitch method.

Further, exposure apparatus main section S may also be a twin-stage type exposure apparatus equipped with a plurality of wafer stages, which is disclosed in, for example, Kokai (Japanese Unexamined Patent Applications Publications) No. 10-163099 and No. 10-214783, and U.S. Pat. No. 6,590,634 corresponding to them, Kohyo (published Japanese translation of International Publication for Patent Application) No. 2000-505958 (and the corresponding U.S. Pat. No. 5,969,441), and the like.

Further, in exposure apparatus main section S of the embodiment above, a light transmissive type mask, which is a light transmissive substrate on which a predetermined light shielding pattern (or a phase pattern or a light attenuation pattern) is formed, is used, but instead of this mask, as is disclosed in, for example, U.S. Pat. No. 6,778,257, an electron mask (which is also called a variable shaped mask, and includes, for example, a DMD (Digital Micromirror Device) that is a type of a non-light-emitting type image display device (which is also called a spatial light modulator) or the like) on which a light-transmitting pattern, a reflection pattern, or a light-emitting pattern is formed according to electronic data of the pattern that is to be exposed may also be used. Further, as is disclosed in, for example, the pamphlet of International Publication No. 2001/035168, the exposure apparatus may also be an exposure apparatus (a lithography system) that forms device patterns on wafer W by forming interference fringes on wafer W.

Further, exposure apparatus main section S may also be a liquid immersion exposure apparatus that performs exposure in a state where the entire surface of wafer W is immersed in liquid as is disclosed in, for example, Kokai (Japanese Unexamined Patent Applications Publications) No. 06-124873, and No. 10-303114, and U.S. Pat. No. 5,825,043, and the like.

Further, in the embodiment above, the exposure apparatus of a local liquid immersion type is exemplified, but part of the substrate processing method and the substrate processing system of the present invention, such as the substrate processing method and the substrate processing system that optimize the inspection conditions based on at least one of a film forming state of a film formed by the film forming apparatus, and film forming conditions of the film forming apparatus, can be applied also to an exposure apparatus that is not a liquid immersion type. Accordingly, the exposure apparatus is not limited to a liquid immersion type.

On the contrary, for example, the liquid immersion monitoring processing is a particular processing that is required in the case where an exposure apparatus is a liquid immersion type, and is not executed in processing using an exposure apparatus that is not a liquid immersion type. Accordingly, to predict the measurement/inspection result using the processing result of the liquid immersion monitoring processing, and hence, to optimize the measurement/inspection processing is required only in the case when an exposure apparatus is a liquid immersion type exposure apparatus.

However, in the device manufacturing plant, since there are non-liquid immersion type exposure apparatuses and liquid immersion type exposure apparatuses together, an operational method, in which the results of such exposure apparatuses of different types are inspected by a common measurement/inspection device, may also be considered. In response to such an operational method, the substrate processing method and the substrate processing system of the present invention may be configured so that the measurement/inspection processing is changed depending on whether a type of the exposure apparatus is a liquid immersion type or not. For example, a configuration may be employed, in which regarding the processing that is not executed in a process using a non-liquid immersion type exposure apparatus, such as the liquid immersion monitoring processing, when the measurement/inspection processing result is predicted, the prediction result can be obtained by omitting a parameter used to reflect the liquid immersion monitoring processing result in the prediction result.

Further, for example, the processing content of the liquid/foreign material removal processing is also different between the case where an exposure apparatus is a liquid immersion type and the case where an exposure apparatus is not a liquid immersion type. To cope with the difference, information as to whether a substrate to which the measurement/inspection processing is to be performed is a substrate processed in a liquid immersion type exposure apparatus or a substrate processed in a non-liquid immersion type exposure apparatus is received, and parameter setting used to predict the measurement/inspection processing result may be adjusted in accordance with the received information.

Further, in the embodiment above, the program related to the present invention is recorded in each flash memory, but the program may also be recorded in other recording media (such as a CD, a magnetooptical disk, a DVD, a memory card, a USB memory, and a floppy disc). Further, the program related to the present invention may also be transferred to each flash memory via a network (such as LAN, intranet, and internet)

Incidentally, the above disclosures of the various publications, the pamphlets of the International Publications, and the U.S. patent application Publications descriptions, and the U.S. patents descriptions that are cited in the embodiment described above and related to exposure apparatuses and the like are each incorporated herein by reference.

While the above-described embodiment of the present invention is the presently preferred embodiment thereof, those skilled in the art of lithography systems will readily recognize that numerous additions, modifications, and substitutions may be made to the above-described embodiment without departing from the spirit and scope thereof. It is intended that all such modifications, additions, and substitutions fall within the scope of the present invention, which is best defined by the claims appended below.

What is claimed is:

1. A substrate processing method of performing a plurality of processing to a substrate using a plurality of processing apparatuses, and inspecting quality of the substrate using at least one inspection device, the method comprising:
   an optimization process of sending information on at least one of a processing result of at least one processing apparatus of the plurality of processing apparatuses and an operating state of the at least one processing apparatus to the at least one inspection device, and optimizing an inspection condition in the at least one inspection device based on the information sent.

2. The substrate processing method according to claim 1, further comprising:
   an adjustment process of predicting that abnormality of the substrate is detected in inspection by the inspection device based on at least one of the processing result of the at least one processing apparatus and the operating state of the at least one processing apparatus, and adjusting a processing condition in the at least one processing apparatus so as to avoid the abnormality.

3. The substrate processing method according to claim 2, wherein
   in the adjustment process of adjusting a processing condition in the at least one processing apparatus, the predicting is made by referring to a correlation acquired in advance between at least one of the processing result of the at least one processing apparatus and the operating state of the at least one processing apparatus, and abnormality detection in the inspection by the inspection device.

4. The substrate processing method according to claim 3, wherein
   the plurality of processing apparatuses include a liquid immersion exposure apparatus that performs liquid immersion exposure to the substrate, and
   the substrate processing method further comprises
   an exposure inspection process of inspecting the substrate to which the liquid immersion exposure has been performed, by using the inspection device; and
   a process of, when it is detected in the exposure inspection process that the substrate has abnormality, adjusting a processing condition in at least one processing apparatus of the plurality of processing apparatuses so as to avoid the abnormality, wherein
   in the optimization process of optimizing an inspection condition, an inspection condition on inspecting the substrate to which the liquid immersion exposure has been performed is optimized based on information on at least one of the processing result and the operating state.

5. The substrate processing method according to claim 4, further comprising:
   a PEB inspection process of inspecting the substrate to which PEB processing has been performed after the liquid immersion exposure, by using the inspection device; and
   a process of, when it is detected in the PEB inspection process that the substrate has abnormality, adjusting a processing condition in at least one processing apparatus of the plurality of processing apparatuses so as to avoid the abnormality, wherein
   in the optimization process of optimizing an inspection condition, an inspection condition on inspecting the substrate to which the PEB processing has been performed is optimized further based on information on at least one of the processing result and the operating state.

6. The substrate processing method according to claim 5, wherein
   in the PEB inspection process, the substrate to which the PEB processing has been performed is inspected by using another inspection device that is different from the inspection device that inspects the substrate to which the liquid immersion exposure has been performed.

7. The substrate processing method according to claim 5, further comprising:
   a development inspection process of inspecting the substrate to which development processing has been performed after the PEB processing, by using the inspection device; and
   a process of, when it is detected in the development inspection process that the substrate has abnormality, adjusting a processing condition in at least one processing apparatus of the plurality of processing apparatuses so as to avoid the abnormality, wherein
   in the optimization process of optimizing an inspection condition, an inspection condition on inspecting the substrate to which the development processing has been performed is optimized further based on information on at least one of the processing result and the operating state.

8. The substrate processing method according to claim 7, wherein
in the development inspection process, the substrate to which the development processing has been performed is inspected by using another inspection device that is different from the inspection device that inspects the substrate to which the liquid immersion exposure has been performed and the inspection device that inspects the substrate to which the PEB processing has been performed.

9. The substrate processing method according to claim 7, further comprising:
a process of obtaining the correlation by using at least one of a processing result of at least one processing apparatus of the plurality of processing apparatuses and an operating state of the at least one processing apparatus, and an inspection result including at least one of a result of the exposure inspection process, a result of the PEB inspection process and a result of the development inspection process.

10. The substrate processing method according to claim 4, wherein
the at least one inspection device includes a pattern inspection device that inspects quality of the substrate based on a pattern formed on the substrate by the liquid immersion exposure.

11. The substrate processing method according to claim 1, wherein
the plurality of processing apparatuses include a film forming apparatus that forms a film on the substrate, and
in the optimization process of optimizing an inspection condition, the inspection condition is optimized based on at least one of a film forming state of a film formed by the film forming apparatus and a film forming condition of the film forming apparatus.

12. The substrate processing method according to claim 11, wherein
the film forming state includes at least one of a film thickness, a variation state of the film thickness, and flatness of the film, and
the film forming condition includes at least one of a film material, a film forming method, a targeted film thickness, film thickness uniformity, film forming environment, and a coating condition of the film material.

13. The substrate processing method according to claim 11, wherein
the film includes at least one of a resist film and a topcoat film.

14. The substrate processing method according to claim 11, further comprising:
an adjustment process of predicting that abnormality of the substrate is detected in inspection by the inspection device based on at least one of the film forming state and the film forming condition, and adjusting the film forming condition in the film forming apparatus so as to avoid the abnormality.

15. The substrate processing method according to claim 14, wherein
in the adjustment process of adjusting the film forming condition, the predicting is made by referring to a correlation between at least one of the film forming state and the film forming condition and abnormality detection in the inspection by the inspection device.

16. The substrate processing method according to claim 1, wherein
the plurality of processing apparatuses include a liquid immersion exposure apparatus that performs liquid immersion exposure to the substrate, and a liquid/foreign material removal device that is arranged on at least one of an inside and an outside of the liquid immersion exposure apparatus and removes at least one of liquid and a foreign material on the substrate, and
in the optimization process of optimizing an inspection condition, the inspection condition is optimized based on at least one of a monitoring result during a sequence of the liquid immersion exposure and a result of removal processing of liquid and a foreign material by the liquid/foreign material removal device that is performed after the liquid immersion exposure.

17. The substrate processing method according to claim 16, further comprising at least one of:
an adjustment process of predicting that abnormality of the substrate is detected in inspection by the inspection device based on the monitoring result during the sequence of the liquid immersion exposure, and adjusting a liquid immersion exposure condition in the liquid immersion exposure apparatus so as to avoid the abnormality; and
a process of removing contamination of an optical element of a projection optical system.

18. The substrate processing method according to claim 17, wherein
in the adjustment process of adjusting a liquid immersion exposure condition, the predicting is made by referring to a correlation acquired in advance between the monitoring result during the sequence of the liquid immersion exposure and abnormality detection in the inspection by the inspection device.

19. The substrate processing method according to claim 17, wherein
the monitoring result includes at least one of foreign material information including at least one of a type, a position, a size, a shape and the number of a foreign material in a liquid immersion area, and optical element contamination information including at least one of a position of contamination of the optical element and a degree of the contamination.

20. The substrate processing method according to claim 17, wherein
the liquid immersion exposure condition includes at least one of a supply condition of liquid, a recovery condition of liquid, a movement condition of the substrate, a size of a liquid immersion area, and a shape of the liquid immersion area.

21. The substrate processing method according to claim 20, wherein
the movement condition of the substrate includes at least one of a movement speed, an acceleration, a deceleration, a movement direction, a movement trajectory, and a movement distance of the substrate with respect to liquid in the liquid immersion area, a time when each position of the substrate is immersed in liquid, and a focus/leveling time.

22. The substrate processing method according to claim 16, further comprising:
an adjustment process of predicting that abnormality of the substrate is detected in inspection by the inspection device based on the result of removal processing of liquid and a foreign material, and adjusting a removal processing condition of at least one of liquid and a foreign material in the liquid/foreign material removal device so as to avoid the abnormality.

23. The substrate processing method according to claim 22, wherein
in the adjustment process of adjusting a removal processing condition of at least one of liquid and a foreign material, the predicting is made by referring to a correlation acquired in advance between the result of removal processing and abnormality detection in the inspection by the inspection device.

24. The substrate processing method according to claim 22, wherein
the removal processing condition of at least one of liquid and a foreign material includes at least one of an on/off condition of a flexure traveling wave, a rotational speed of the substrate, a tilt angle of the substrate, a blowing condition of gas, a suction condition of liquid, and a drying condition of liquid in the liquid/foreign material removal device.

25. The substrate processing method according to claim 16, wherein
the at least one inspection device includes a pattern inspection device that inspects quality of the substrate based on a pattern formed on the substrate by the liquid immersion exposure.

26. The substrate processing method according to claim 1, wherein
the inspection condition includes at least one of an area subject to inspection on the substrate and inspection sensitivity of the inspection device.

27. The substrate processing method according to claim 26, wherein
the at least one inspection device includes a pattern inspection device that inspects quality of the substrate based on a pattern formed on the substrate by the liquid immersion exposure.

28. The substrate processing method according to claim 1, wherein
the at least one inspection device includes an appearance inspection device that inspects quality of the substrate based on appearance of the substrate.

29. A substrate processing method of performing a plurality of processing to a substrate using a plurality of processing apparatuses that include a liquid immersion exposure apparatus that performs liquid immersion exposure to the substrate and a liquid/foreign material removal device that is arranged on at least one of an inside and an outside of the liquid immersion exposure apparatus and removes at least one of liquid and a foreign material on the substrate, and inspecting quality of the substrate using at least one inspection device, the method comprising:
a process of judging whether or not there is a possibility that at least one of liquid and a foreign material on the substrate adversely affects the substrate, based on a result obtained by inspecting a removal processing result of the liquid and the foreign material by the inspection device;
a process of sending result information of the judgment to the liquid/foreign material removal device; and
a process of performing removal processing of at least one of the liquid and the foreign material again in accordance with the result information of the judgment sent, when a result of the judgment shows that there is a possibility that at least one of the liquid and the foreign material on the substrate adversely affects the substrate.

30. The substrate processing method according to claim 29, wherein
the at least one inspection device includes a pattern inspection device that inspects quality of the substrate based on a pattern formed on the substrate by the liquid immersion exposure.

31. The substrate processing method according to claim 29, wherein
the at least one inspection device includes an appearance inspection device that inspects quality of the substrate based on appearance of the substrate.

32. A substrate processing method of performing a plurality of processing to a substrate using a plurality of processing apparatuses that include a liquid immersion exposure apparatus that performs liquid immersion exposure to the substrate and a liquid/foreign material removal device that is arranged on at least one of an inside and an outside of the liquid immersion exposure apparatus and removes at least one of liquid and a foreign material on the substrate, and inspecting quality of the substrate using at least one inspection device, the method comprising:
a process of judging whether or not there is a possibility that at least one of liquid and a foreign material on the substrate adversely affects the substrate, based on a result obtained by inspecting a removal processing result of the liquid and the foreign material by the inspection device; and
a process of notifying the liquid/foreign material removal device, when a result of the judgment shows that there is a possibility that at least one of the liquid and the foreign material on the substrate adversely affects the substrate.

33. The substrate processing method according to claim 32, wherein
the at least one inspection device includes a pattern inspection device that inspects quality of the substrate based on a pattern formed on the substrate by the liquid immersion exposure.

34. The substrate processing method according to claim 32, wherein
the at least one inspection device includes an appearance inspection device that inspects quality of the substrate based on appearance of the substrate.

35. A substrate processing system, comprising:
a plurality of processing apparatuses that respectively perform a plurality of processing to a substrate; and
at least one inspection device that inspects quality of the substrate, wherein
the at least one inspection device receives information on at least one of a processing result of at least one processing apparatus of the plurality of processing apparatuses and an operating state of the at least one processing apparatus, and optimizes an inspection condition based on the information received.

36. The substrate processing system according to claim 35, further comprising:
an adjustment instructing device that makes prediction that abnormality of the substrate is detected in inspection by the inspection device based on at least one of the processing result of the at least one processing apparatus and the operating state of the at least one processing apparatus, and instructs the at least one processing apparatus to adjust a processing condition so as to avoid the abnormality.

37. The substrate processing system according to claim 36, wherein
the adjustment instructing device makes the prediction by referring to a correlation acquired in advance between at least one of the processing result of the at least one processing apparatus and the operating state of the at least one processing apparatus, and abnormality detection in the inspection by the inspection device.

38. The substrate processing system according to claim 37, wherein
the plurality of processing apparatuses include a liquid immersion exposure apparatus that performs liquid immersion exposure to the substrate,
the at least one inspection device includes an exposure inspection device that inspects the substrate to which the liquid immersion exposure has been performed,
when it is detected by the exposure inspection device that the substrate has abnormality, the adjustment instructing device further instructs at least one processing apparatus of the plurality of processing apparatuses to adjust a processing condition so as to avoid the abnormality, and
the exposure inspection device optimizes an inspection condition based on information on at least one of the processing result and the operating state.

39. The substrate processing system according to claim 38, wherein
the at least one inspection device includes a PEB inspection device that inspects the substrate to which PEB processing has been performed,
when it is detected by the PEB inspection device that the substrate has abnormality, the adjustment instructing device further instructs at least one processing apparatus of the plurality of processing apparatuses to adjust a processing condition so as to avoid the abnormality, and
the PEB inspection device optimizes an inspection condition based on information on at least one of the processing result and the operating state.

40. The substrate processing system according to claim 39, wherein
the at least one inspection device includes a development inspection device that inspects the substrate to which development processing has been performed,
when it is detected by the development inspection device that the substrate has abnormality, the adjustment instructing device further instructs at least one processing apparatus of the plurality of processing apparatuses to adjust a processing condition so as to avoid the abnormality, and
the development inspection device optimizes an inspection condition based on information on at least one of the processing result and the operating state.

41. The substrate processing system according to claim 40, wherein
the adjustment instructing device further obtains the correlation by using at least one of a processing result of at least one processing apparatus of the plurality of processing apparatuses and an operating state of the at least one processing apparatus, and an inspection result including at least one of an inspection result of the exposure inspection device, an inspection result of the PEB inspection device and an inspection result of the development inspection device.

42. The substrate processing system according to claim 38, wherein
the at least one inspection device includes a pattern inspection device that inspects quality of the substrate based on a pattern formed on the substrate by the liquid immersion exposure.

43. The substrate processing system according to claim 35, wherein
the plurality of processing apparatuses include a film forming apparatus that forms a film on the substrate, and
the at least one inspection device optimizes the inspection condition based on at least one of a film forming state of a film formed by the film forming apparatus and a film forming condition of the film forming apparatus.

44. The substrate processing system according to claim 43, wherein
the film forming state includes at least one of a film thickness, a variation state of the film thickness, and flatness of the film, and
the film forming condition includes at least one of a film material, a film forming method, a targeted film thickness, film thickness uniformity, film forming environment, and a coating condition of the film material.

45. The substrate processing system according to claim 43, wherein
the film includes at least one of a resist film and a topcoat film.

46. The substrate processing system according to claim 43, further comprising:
an adjustment instructing device that makes prediction that abnormality of the substrate is detected in inspection by the inspection device based on at least one of the film forming state and the film forming condition, and instructs the film forming apparatus to adjust the film forming condition so as to avoid the abnormality.

47. The substrate processing system according to claim 46, wherein
the adjustment instructing device makes the prediction by referring to a correlation acquired in advance between at least one of the film forming state and the film forming condition and abnormality detection in the inspection by the inspection device.

48. The substrate processing system according to claim 35, wherein
the plurality of processing apparatuses include a liquid immersion exposure apparatus that performs liquid immersion exposure to the substrate, and a liquid/foreign material removal device that is arranged on at least one of an inside and an outside of the liquid immersion exposure apparatus and removes at least one of liquid and a foreign material on the substrate, and
the at least one inspection device optimizes the inspection condition based on at least one of a monitoring result during a sequence of the liquid immersion exposure and a result of removal processing of liquid and a foreign material by the liquid/foreign material removal device that is performed after the liquid immersion exposure.

49. The substrate processing system according to claim 48, further comprising at least one of:
an adjustment instructing device that makes prediction that abnormality of the substrate is detected in inspection by the at least one inspection device based on the monitoring result during the sequence of the liquid immersion exposure, and instructs the liquid immersion exposure apparatus to adjust a liquid immersion exposure condition so as to avoid the abnormality; and
a device that instructs contamination removal of an optical element of a projection optical system.

50. The substrate processing system according to claim 49, wherein
the adjustment instructing device makes the prediction by referring to a correlation acquired in advance between the monitoring result during the sequence of the liquid immersion exposure and abnormality detection in the inspection by the inspection device.

51. The substrate processing method according to claim 49, wherein
the monitoring result includes at least one of foreign material information including at least one of a type, a position, a size, a shape and the number of a foreign material in a liquid immersion area, and optical element contamination information including at least one of a position of contamination of the optical element and a degree of the contamination.

52. The substrate processing system according to claim 49, wherein
the liquid immersion exposure condition includes at least one of a supply condition of liquid, a recovery condition of liquid, a movement condition of the substrate, a size of a liquid immersion area, and a shape of the liquid immersion area.

53. The substrate processing system according to claim 52, wherein
the movement condition of the substrate includes at least one of a movement speed, an acceleration, a deceleration, a movement direction, a movement trajectory, and a movement distance of the substrate with respect to liquid in the liquid immersion area, a time when each position of the substrate is immersed in liquid, and a focus/leveling time.

54. The substrate processing system according to claim 48, further comprising:
an adjustment instructing device that makes prediction that abnormality of the substrate is detected in inspection by the inspection device based on the result of removal processing of liquid and a foreign material, and instructs the liquid/foreign material removal device to adjust a removal processing condition of at least one of liquid and a foreign material so as to avoid the abnormality.

55. The substrate processing system according to claim 54, wherein
the adjustment instructing device makes the prediction by referring to a correlation acquired in advance between the result of removal processing and abnormality detection in the inspection by the inspection device.

56. The substrate processing system according to claim 54, wherein
the removal processing condition of at least one of liquid and a foreign material includes at least one of an on/off condition of a flexure traveling wave, a rotational speed of the substrate, a tilt angle of the substrate, a blowing condition of gas, a suction condition of liquid, and a drying condition of liquid in the liquid/foreign material removal device.

57. The substrate processing system according to claim 48, wherein
the at least one inspection device includes a pattern inspection device that inspects quality of the substrate based on a pattern formed on the substrate by the liquid immersion exposure.

58. The substrate processing system according to claim 35, wherein
the inspection condition includes at least one of an area subject to inspection on the substrate and inspection sensitivity of the inspection device.

59. The substrate processing system according to claim 58, wherein
the at least one inspection device includes a pattern inspection device that inspects quality of the substrate based on a pattern formed on the substrate by the liquid immersion exposure.

60. The substrate processing system according to claim 35, wherein
the at least one inspection device includes an appearance inspection device that inspects quality of the substrate based on appearance of the substrate.

61. A substrate processing system, comprising:
a liquid immersion exposure apparatus that performs liquid immersion exposure to a substrate;
a liquid/foreign material removal device that is arranged on at least one of an inside and an outside of the liquid immersion exposure apparatus and removes at least one of liquid and a foreign material on the substrate to which the liquid immersion exposure has been performed;
an inspection device that inspects the substrate to which removal processing of at least one of liquid and a foreign material has been performed by the liquid/foreign material removal device; and
a judgment device that judges whether or not there is a possibility that at least one of liquid and a foreign material on the substrate adversely affects the substrate based on an inspection result of the inspection device, and sends result information of the judgment to the liquid/foreign material removal device, wherein
when there is a possibility that at least one of the liquid and the foreign material on the substrate adversely affects the substrate, the liquid/foreign material removal device performs removal processing of at least one of the liquid and the foreign material again in accordance with the result information of the judgment sent.

62. The substrate processing system according to claim 61, wherein
the at least one inspection device includes a pattern inspection device that inspects quality of the substrate based on a pattern formed on the substrate by the liquid immersion exposure.

63. The substrate processing system according to claim 61, wherein
the at least one inspection device includes an appearance inspection device that inspects quality of the substrate based on appearance of the substrate.

64. A substrate processing system, comprising:
a liquid immersion exposure apparatus that performs liquid immersion exposure to a substrate;
a liquid/foreign material removal device that is arranged on at least one of an inside and an outside of the liquid immersion exposure apparatus and removes at least one of liquid and a foreign material on the substrate to which the liquid immersion exposure has been performed;
an inspection device that inspects the substrate to which removal processing of at least one of liquid and a foreign material has been performed by the liquid/foreign material removal device; and
a judgment device that judges whether or not there is a possibility that at least one of liquid and a foreign material on the substrate adversely affects the substrate based on an inspection result of the inspection device, and notifies the liquid/foreign material removal device when a result of the judgment shows that there is a possibility that at least one of the liquid and the foreign material on the substrate adversely affects the substrate.

65. The substrate processing system according to claim 64, wherein the at least one inspection device includes a pattern inspection device that inspects quality of the substrate based on a pattern formed on the substrate by the liquid immersion exposure.

66. The substrate processing system according to claim 64, wherein the at least one inspection device includes an appearance inspection device that inspects quality of the substrate based on appearance of the substrate.

67. A measurement/inspection apparatus that inspects quality of a substrate that has been processed by a plurality of processing apparatuses, the apparatus comprising:

a receiving section that receives information on at least one of a processing result of at least one processing apparatus of the plurality of processing apparatuses and an operating state of the at least one processing apparatus, whereby an inspection condition is optimized based on the information received.

68. The measurement/inspection apparatus according to claim 67, wherein the plurality of processing apparatuses include a film forming apparatus that forms a film on the substrate, and based on at least one of a film forming state of a film formed by the film forming apparatus and a film forming condition of the film forming apparatus, the inspection condition is optimized.

69. The measurement/inspection apparatus according to claim 67, wherein the plurality of processing apparatuses include a liquid immersion exposure apparatus that performs liquid immersion exposure to the substrate and a liquid/foreign material removal device that is arranged on at least one of an inside and an outside of the liquid immersion exposure apparatus and removes liquid/foreign material on the substrate, and based on at least one of a monitoring result during a sequence of the liquid immersion exposure and a result of removal processing of liquid/foreign material by the liquid/foreign material removal device that is performed after the liquid immersion exposure, the inspection condition is optimized.

* * * * *